(12) United States Patent
Bianco et al.

(10) Patent No.: US 7,858,648 B2
(45) Date of Patent: Dec. 28, 2010

(54) NON-COVALENT COMPLEXES COMPRISING CARBON NANOTUBES

(75) Inventors: Alberto Bianco, Strasbourg (FR); Davide Pantarotto, Porcia (IT); Kostas Kostarelos, London (GB); Maurizio Prato, Trieste (IT)

(73) Assignees: Centre National de la Recherche Scientifique (C.N.R.S.), Paris (FR); University of London, The School of Pharmacy, London (GB); Universita degli Studi di Trieste, Trieste (IT)

( * ) Notice: Subject to any disclaimer, the term of this patent is extended or adjusted under 35 U.S.C. 154(b) by 634 days.

(21) Appl. No.: 11/628,749

(22) PCT Filed: Jun. 6, 2005

(86) PCT No.: PCT/EP2005/006036

§ 371 (c)(1),
(2), (4) Date: Sep. 13, 2007

(87) PCT Pub. No.: WO2005/121799

PCT Pub. Date: Dec. 22, 2005

(65) Prior Publication Data

US 2008/0076816 A1    Mar. 27, 2008

(30) Foreign Application Priority Data

Jun. 9, 2004   (EP)   .................. 04291440

(51) Int. Cl.
| | | |
|---|---|---|
| C07D 207/12 | (2006.01) | |
| C07D 207/08 | (2006.01) | |
| C07D 213/64 | (2006.01) | |
| C07D 213/76 | (2006.01) | |
| A61K 31/4025 | (2006.01) | |
| A61K 31/4015 | (2006.01) | |
| A61K 31/4439 | (2006.01) | |

(52) U.S. Cl. .................... 514/343; 514/422; 546/276.4; 548/518; 977/746; 977/748; 977/750; 977/752

(58) Field of Classification Search ...................... None
See application file for complete search history.

(56) References Cited

FOREIGN PATENT DOCUMENTS

| WO | WO 99/57564 | 11/1999 |
|---|---|---|
| WO | WO 2004/089818 | 10/2004 |
| WO | WO 2004/089819 | 10/2004 |

OTHER PUBLICATIONS

Adv. Mater. 15(20), pp. 1765-1768 (Oct. 16, 2003).*
Pantarotto, et al. Angew. Chem. Int. Ed. 43:5242 (2004).*
Singh, et al. J. Am. Chem. Soc. 127:4388 (2005).*
Bianco, et al. Adv. Mat. 15:1765 (2003).*
Georgakilas V et al.:, "Amino Acid Functionalisation of Water Soluble Carbon Nanotubes", Chemical Communications—Chemcom, Royal Society of Chemistry, GB, Nov. 14, 2002, pp. 3050-3051, XP002265590, ISSN: 1359-7345, The Whole Document.
Georgakilas V et al.:, "Organic Functionalized Carbon Nanotubes", Proceedings of the International Winterschool on Electronic Properties of Mar. 2, 2002, pp. 73-76, XP002262087, Cited in the Application the Whole Page.

* cited by examiner

Primary Examiner—Rebecca L Anderson
Assistant Examiner—Michael Barker
(74) Attorney, Agent, or Firm—Young & Thompson

(57) ABSTRACT

The present invention relates to the use of a carbon nanotube comprising positive and/or negative charges, the charges being carried by at least one charge-carrying group, the charge carrying group being covalently bound to the surface of the carbon nanotube, for the manufacture of a complex between the carbon nanotube and at least one charged molecule, the bond between the carbon nanotube and the charged molecule being essentially electrostatic, and the charged molecule comprising at least one negative charge if the carbon nanotube comprises positive charges and/or at least one positive charge if the carbon nanotube comprises negative charges.

42 Claims, 13 Drawing Sheets

A. SWNT-NH$_3^+$

B. SWNT-Lys-NH$_3^+$

C. MWNT-NH$_3^+$

NON-COVALENT COMPLEXES COMPRISING CARBON NANOTUBES

The present invention relates to non-covalent complexes comprising carbon nanotubes and to their use for the delivery of molecules into cells.

Due to their exceptional combination of mechanical, thermal, chemical, and electronic properties, single-walled (SWNT) and multi-walled carbon nanotubes (MWNT) are considered as unique materials, with very promising future applications, especially in the field of nanotechnology, nano-electronics, composite materials and medicinal chemistry.

However, so far, potential biological applications of carbon nanotubes (CNT) have been very little explored, mainly because of their lack of solubility in physiological solutions.

Several non-covalent complexes between carbon nanotubes and various molecules, such as DNA or proteins, have been described in the prior art. In most instances, the molecules and the carbon nanotubes are bound together through hydrophobic and/or π-stacking interactions.

Thus, Zheng et al. (2003) *Nature Mater.* 2:338-342 describe the solubilization of carbon nanotubes by single stranded DNA molecules, wherein the DNA molecule wraps helically around the carbon nanotube through π-stacking interactions to form a soluble complex.

In another instance, WO 02/095099 relates to complexes formed from the irreversible adsorption of molecules, possibly comprising proteins or DNA, to the sidewalls of carbon nanotubes through π-stacking, van der Waals and hydrophobic interactions.

One drawback associated with such complexes is that the dissociation of the complex is either difficult and/or has not been soundly assessed.

Another drawback associated to those complexes is that once dissociated from the complex, the carbon nanotube by itself is not soluble in aqueous systems and tends to form hydrophobic aggregates which precipitate. Besides, non functionalized carbon nanotubes have been shown to be toxic in several instances (Warheit et al. (2004) *Toxicological Sciences* 77:117-125; Lam et al. (2004) *Toxicological Sciences* 77:126-134; Shvedova et al. (2003) *Journal of Toxicology and Environmental Health, Part A* 66:1909-1926).

Such drawbacks severely impair the ability of these non-covalent complexes to be used for the delivery, in biological systems, of the molecules complexed to the carbon nanotubes.

Furthermore, it has never been demonstrated that complexes such as described above could penetrate into cells.

Thus, it is an object of the present invention to provide complexes comprising carbon nanotubes and molecules of interest and being liable to release said molecules of interest.

It is another object of the present invention to provide complexes comprising carbon nanotubes in which the carbon nanotube is soluble by itself.

It is a further object of the present invention to provide biologically compatible and non-toxic complexes comprising carbon nanotubes which are capable to penetrate into cells.

It is another object of the invention to provide a process for preparing complexes comprising carbon nanotubes presenting the above mentioned properties.

The present invention relates to the use of a carbon nanotube comprising positive and/or negative charges, said charges being carried by at least one charge-carrying group, said charge-carrying group being covalently bound to the surface of said carbon nanotube, for the manufacture of a complex between said carbon nanotube and at least one charged molecule, provided that the charged molecule is different from $Cl^-$ and $TFA^-$, the bond between the carbon nanotube and the charged molecule being essentially electrostatic, and said charged molecule comprising at least one negative charge if said carbon nanotube comprises positive charges and/or at least one positive charge if said carbon nanotube comprises negative charges.

The present invention also relates to the use of a carbon nanotube comprising positive and/or negative charges, said charges being carried by at least one charge-carrying group, said charge-carrying group being covalently bound to the surface of said carbon nanotube, for the manufacture of a complex between said carbon nanotube and at least one charged molecule having a molecular weight greater than about 115, the bond between the carbon nanotube and the charged molecule being essentially electrostatic, and said charged molecule comprising at least one negative charge if said carbon nanotube comprises positive charges and/or at least one positive charge if said carbon nanotube comprises negative charges.

The present invention also relates to a complex comprising:

a carbon nanotube comprising positive and/or negative charges, said charges being carried by at least one charge-carrying group, said charge-carrying group being covalently bound to the surface of said carbon nanotube, and at least one charged molecule, said charged molecule comprising at least one negative charge if said carbon nanotube comprises positive charges and/or at least one positive charge if said carbon nanotube comprises negative charges, provided that the charged molecule is different from $Cl^-$ and $TFA^-$, the bond between the carbon nanotube and the charged molecule being essentially electrostatic.

The present invention also relates to a complex comprising:

a carbon nanotube comprising positive and/or negative charges, said charges being carried by at least one charge-carrying group, said charge-carrying group being covalently bound to the surface of said carbon nanotube, and at least one charged molecule having a molecular weight greater than about 115, said charged molecule comprising at least one negative charge if said carbon nanotube comprises positive charges and/or at least one positive charge if said carbon nanotube comprises negative charges, the bond between the carbon nanotube and the charged molecule being essentially electrostatic.

The expression "carbon nanotubes" refers to molecules constituted only of carbon atoms arranged in a cylinder, said cylinder being characterized by a defined length and diameter. The carbon nanotube is similar to a rolled up graphite plane, thus forming a graphite cylinder; the side-wall carbon atoms of the cylinder are arranged in order to form fused benzene rings, as in planar graphite.

The expression "charge-carrying group" designates a group carrying at least one charge. The charge-carrying group can carry only positive charges, only negative charges or both. Furthermore, the charge-carrying group can comprise more positive charges than negative charges; its net, or global, charge is then positive; conversely the charge-carrying group can comprise more negative charges than positive charges; its net, or global, charge is then negative. The charge-carrying group can also comprise an equal amount of positive and negative charges; its net, or global, charge is then neutral.

The expression "charged molecule" designates a molecule carrying at least one charge. The charged molecule can carry only positive charges, only negative charges or both. Furthermore, the charged molecule can comprise more positive charges than negative charges; its net, or global, charge is then positive; conversely the charged molecule can comprise more negative charges than positive charges; its net, or global, charge is then negative. The charged molecule can also comprise an equal amount of positive and negative charges; its net, or global, charge is then neutral.

According to the invention, a charge-carrying group is covalently linked to the surface of carbon nanotubes by bonds involving at least one of the carbon atoms pertaining to the side-walls of the carbon nanotube. The carbon nanotube can be said to be functionalized by the charge-carrying group.

"TFA-" relates to trifluoroacetic acid.

The force which maintains the cohesion of the complex according to the invention is essentially of electrostatic nature, i.e. the cohesion of the complex is maintained by the attraction which is exerted upon one another by charges of opposite polarity respectively belonging to the charge-carrying group and to the charged molecule. An electrostatic bond according to the invention particularly relates to an ionic bond. It will be clear to anyone skilled in the art that one or more charges belonging to the charge-carrying group can interact respectively with one or more charge belonging to the charged molecule. It will also be clear that when a charge-carrying group, or a charged molecule, comprises more than one charge, not all charges necessarily interact with charges respectively belonging to a charged molecule, or a to charge-carrying group.

Depending on the conditions, such as the pH, the charge of the carbon nanotube, of the charge-carrying group or of the charged molecule can vary.

According to a preferred embodiment of the invention, the above defined complex is characterized in that it is soluble in aqueous solvents and non-toxic.

In particular the complex is soluble in water for concentrations from $1.10^{-2}$ to $1.10^{12}$ mol/l.

Aqueous solvents comprise in particular water, physiological solutions and biological fluids, such as blood, lymph or cytoplasm.

By "non-toxic", it is meant that the complex according to the invention produces essentially no harmful effects to cells or to individuals to whom it is administered.

In particular the complex according to the invention is non-toxic even at concentrations as high as $1.10^{-2}$ mol/l.

The carbon nanotubes involved in the complexes according to the invention are preferably soluble in aqueous solvents and non-toxic.

The solubility of the complex is due to the presence of charge-carrying groups covalently bound to the surface of carbon nanotubes, as well as to the presence of the charged molecules. The solubility of the complex also prevents toxicity due to the hydrophobic aggregation of carbon nanotubes which could impair biological, and in particular cellular, processes.

The solubility and the lack of toxicity of the complex enable its administration to living organisms, in particular in the frame of molecular delivery into cells.

According to another preferred embodiment of the invention, the above defined complex is characterized in that the binding energy between a charged molecule and the carbon nanotube is lower than about 90 kJ/mol, and is in particular from about 12 kJ/mol to about 85 kJ/mol, more particularly from about 20 kJ/mol to about 70 kJ/mol, and preferably from about 20 kJ/mol to about 50 kJ/mol.

The above mentioned binding energies are expressed at 25° C.

A binding energy of 85 kJ/mol corresponds to a dissociation constant of approximately $10^{-15}$ mol/l.

A binding energy of 70 kJ/mol corresponds to a dissociation constant of approximately $10^{-12}$ mol/l.

A binding energy of 50 kJ/mol corresponds to a dissociation constant of approximately $10^{-9}$ mol/l.

In particular, the above mentioned binding energies are weaker than the binding energy corresponding to covalent bonds, which is around 420 kJ/mol.

Preferably, the binding energy between the charged molecule and the carbon nanotube is such that it can enable the cohesion of the complex in extracellular biological fluids, such a blood or lymph, and its dissociation in cellular fluids, such as cytoplasm, enabling the release of the charged molecule. The dissociation of the complex according to the invention can be induced, for instance, by a change in pH.

According to a further preferred embodiment of the above defined complex, the carbon nanotube comprises either positive charges or negative charges and the charged molecule comprises respectively either at least one negative charge or at least one positive charge.

According to this embodiment, the carbon nanotube contains either only positive charges or only negative charges, which facilitates the binding of charged molecules respectively containing opposite charges.

According to a particularly preferred embodiment the carbon nanotube contains only identical charge-carrying groups.

According to another preferred embodiment of the above defined complex, the carbon nanotube comprises from about 0.001 to about 100 charges, in particular from about 1 to about 20 charges, per charge of the charged molecule.

Accordingly, it is possible to modulate the strength of the interaction between a given charged molecule and carbon nanotubes by modifying the charge density of said carbon nanotubes. Thus, increasing the charge density results in a strengthening of the interaction, and decreasing the charge density results in a weakening of the interaction.

The carbon nanotube: charged molecule charge ratio is from about 0.001 to about 100, in particular from about 1 to about 20. For a charge ratio smaller than about 0.001, there is an excess amount of charges from the charged molecule that remains free in solution, leading to an excess of charged molecules not interacting with the carbon nanotubes, therefore not adequately complexed. For a charge ratio higher than 100, there is an excess amount of charges onto the carbon nanotube, therefore the charged molecules are all tightly complexed onto the carbon nanotube surface, thus leading to a strong complex stability, therefore making the release of the charged molecule from the carbon nanotube surface difficult.

According to another preferred embodiment of the above defined complex, the carbon nanotube is substantially intact and soluble in organic and/or aqueous solvents in the presence or absence of the charged molecule, and the charge-carrying groups are homogeneously distributed on the surface of said carbon nanotube.

The expression "homogeneously distributed" means that the charge-carrying groups are statistically distributed all along the surface of the carbon nanotube and not simply concentrated on a part of it, such as the extremities of the carbon nanotube. In addition, there is a ratio between the number of charge-carrying groups and the number of carbon atom of the carbon nanotube, in particular there is 1 charge-carrying group per about 50 to about 1000 carbon atoms of the carbon nanotube, more particularly there is 1 charge-carrying group per about 100 carbon atoms of the carbon nanotube.

The expression "substantially intact" means that there is a very low amount of defects on the surface, and no shortening of the carbon nanotubes, due to the oxidation of the carbon atoms of the extremities of the carbon nanotubes into carboxylic acids.

In particular, the carbon nanotube is by itself soluble in aqueous solvents, notably in biological fluids, such as blood, lymph or cytoplasm. Thus the dissociation of the complex according to the invention yields two aqueously soluble components, the charged molecule and the carbon nanotube. When the dissociation occurs in a cell, the carbon nanotube remains soluble, which favors its discarding from said cell and prevents its aggregation and the cytotoxicity corresponding to aggregation.

According to still another preferred embodiment of the above defined complex, the carbon nanotube is a single-walled (SWNT) or a multi-walled carbon nanotube (MWNT).

The single-walled carbon nanotubes (SWNT) are for instance defined in Ajayan, P M & Iijima S, *Nature* (1993) 361:333-334; Rao C N R. et al. *Chem. Phys. Chem.* (2001) 2:78-105.

The multi-walled carbon nanotubes are for instance defined in Iijima, S. *Nature* (1991) 354:56-58; Rao C N R. et al. *Chem. Phys. Chem.* (2001) 2:78-105.

According to a further preferred embodiment of the above defined complex, the carbon nanotube corresponds to the following general formula:

$$[C_n]-X_m$$

wherein:
- $C_n$ are surface carbons of a substantially cylindrical carbon nanotube of substantially constant diameter, said diameter being from about 0.5 to about 50 nm, in particular from about 0.5 to 5 nm for SWNT and from about 20 to about 50 nm for MWNT,
- X represents one or several functional groups, identical or different, provided that at least one of the X groups comprises at least one charge-carrying group,
- n is an integer from about $3.10^{3'}$ to about $3.10^6$,
- m is an integer from about 0.001 n to about 0.1 n, there are from about $2.10^{-11}$ moles to about $2.10^{-9}$ moles of X functional groups per cm² of carbon nanotube surface, The carbon nanotubes include those having a length to diameter ratio greater than 5 and a diameter of less than 0.2 μm, preferably less than 0.05 μm.

In substituted carbon nanotubes, the surface atoms $C_n$ react with the functional groups. Most carbon atoms in the surface layer are basal plane carbons, such as carbons constitutive of benzene rings. In the prior art, basal plane carbons are generally considered to be relatively inert to chemical attack, except those which stand at defect sites or which are analogous to the edge carbon atoms of a graphite plane.

The carbon atoms of the extremities of carbon nanotubes may include carbon atoms exposed at defects sites and edge carbon atoms.

According to an advantageous embodiment, the invention relates to an aqueous or organic solution containing functionalized carbon nanotubes wherein the distribution of the length range of the carbon nanotubes is substantially the same as the distribution of the length range of the carbon nanotubes before functionalization.

The length of the carbon nanotubes is advantageously chosen in the range from about 20 nm to about 20 μm.

The distribution of functional groups per cm² of carbon nanotube surface which is advantageously of $2.10^{-11}$ moles to $2.10^{-9}$ moles can be determined by DSC (differential scanning calorimetry), TGA (thermo gravimetric assay), titrations and spectrophotometric measurements.

Its homogeneity can be determined by high resolution transmission electron microscopy (TEM), provided the resolution is sufficient to see the electron density of the carbon nanotube surface and of the functional groups it carries, or by NMR (nuclear magnetic resonance) spectroscopy, provided labelled atoms, such as $^{15}N$, $^{13}C$ or $^{2}H$, are present in functional groups.

The parameters involved in the higher and lower values of the range of the distribution of functional groups per cm² of carbon nanotube surface are the curvature of the carbon nanotube, the reaction time, the temperature of the reaction, the chemical stability of the reagents and the solvent.

Preferably, the quantity of functional groups ranges in particular from about 0.4 to about 1 mmol/g of carbon nanotube.

The carbon nanotubes of the invention are substantially pure and do not contain amorphous or pyrolytically deposited carbon, carbon particles, or fullerenes, and are in particular devoid of metals such as Fe, Ni, Co, that are generally used as catalysts in the production of carbon nanotubes.

In a preferred embodiment of the above defined complex, X represents two different functional groups, $X^1$ and $X^2$, and the carbon nanotube corresponds to the following formula:

$$[C_n]-[X^1_{m1}][X^2_{m2}]$$

wherein, independently from each other, $m_1$ and $m_2$ represent integers from about 0.001 n to about 0.1 n, provided that at least one of $X^1$ or $X^2$ comprises at least one charge-carrying group.

In another preferred embodiment of the above defined complex, X represents one or several substituted pyrrolidine rings, identical or different, provided that at least one of said substituted pyrrolidine rings is substituted by at least one charge-carrying group, of the following general formula (I):

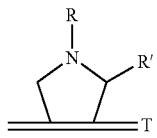

I wherein T represents a carbon nanotube, and independently from each other R and R' represent —H or a group of formula -M-Y—$(Z)_a$—$(P)_b$, wherein a represents 0 or 1 and b represents an integer from 0 to 8, preferably 0, 1, or 2, P representing identical or different groups when b is greater than 1, provided R and R' cannot simultaneously represent H, and:

M is a spacer group from about 1 to about 100 atoms, if appropriate comprising a charge-carrying group, such as a group selected from the list comprising —$(CH_2)_r$—, or —$(CH_2$—$CH_2$—$O)_r$—$CH_2$—$CH_2$—, wherein r is an integer from 1 to 20, Y is a reactive group when a=b=0, if appropriate comprising a charge-carrying group, such as a group selected from the list comprising —OH, —$NH_3^+$, —COO⁻, —SH, —CHO, a ketone such as —$COCH_3$, an azide or a halide.

or derived from a reactive group, when a or b is different from 0, if appropriate charged, such as a group selected from the list comprising —O—, —NH—, —COO—, —S—, —CH=, —$CH_2$—, —$CC_kH_{2k+1}$=, wherein k is an integer from 1 to 10, in particular —$CCH_3$=, or —$CHC_kH_{2k+1}$—, wherein k is an integer from 1 to 10, in particular —$CHCH_3$—;

Z is a linker group, if appropriate comprising a charge-carrying group, liable to be linked to at least one P group, and if need be to release said P group, such as a group of one of the following formulae when a=1 and b=0:

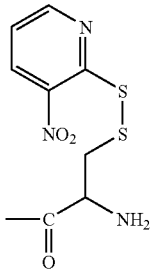

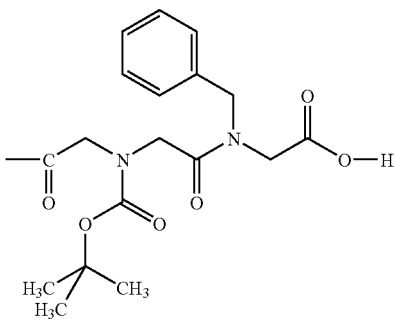

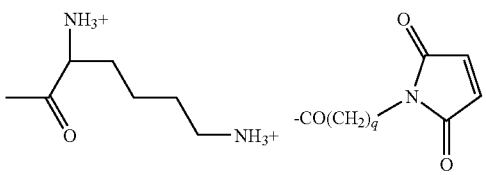

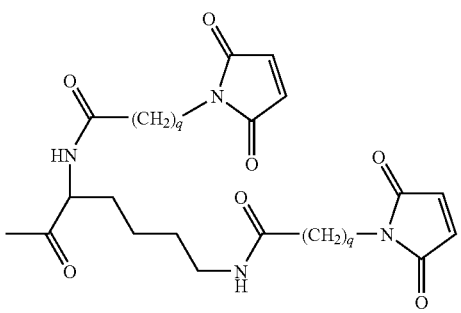

wherein q is an integer from 1 to 10;
or of one of the corresponding following formulae when a=1 and b=1 or 2:

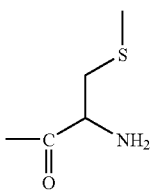

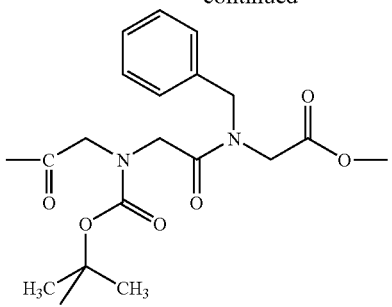

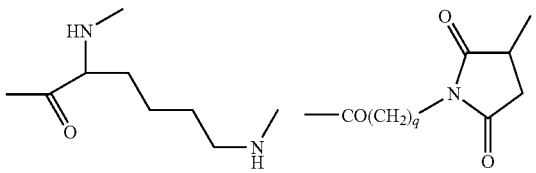

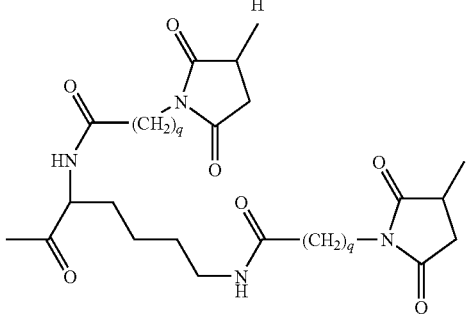

wherein q is an integer from 1 to 10;

P is an effective group, if appropriate comprising a charge-carrying group, allowing spectroscopic detection of said functionalized carbon nanotube, such as a fluorophore, such as FITC, a chelating agent, such as DTPA, or an active molecule, liable to induce a biological effect, such as an amino acid, a peptide, a pseudopeptide, a polypeptide, a protein, such as an enzyme or an antibody, a nucleic acid, a carbohydrate, or a drug.

if appropriate at least one of Y, Z, or P groups, can be substituted by a capping group, such as $CH_3CO$—(acetyl), methyl, ethyl, or benzylcarbonyl, or a protecting group such as methyl, ethyl, benzyl, tert-butyl, trityl, 3-nitro-2-pyridylsulfenyl, tert-butyloxycarbonyl (Boc), fluorenylmethyloxycarbonyl (Fmoc), benzyloxycarbonyl (Cbz), benzoyl (Bz), trimethylsilylethyloxycarbonyl, phtalimide, dimethylacetal, diethylacetal or, 1,3-dioxolane.

Carbon nanotubes comprising substituted pyrrolidine can be prepared using the general method based on the 1,3-dipolar cycloaddition of azomethine ylides as described in Georgakilas et al. (2002) *J. Am. Chem. Soc.* 124:760-761.

The pyrrolidine ring has the advantage of being a stable and robust cyclic molecule, presenting a nitrogen atom which can bear a spacer group at the end of which a reactive group can be present or inserted.

The expression "Y is a reactive group" means that Y represents a heteroatom, ready to undertake a chemical reaction to form a new covalent bond.

The expression "M is a spacer group" means that M is a linear organic chain which keeps separate the pyrrolidine on the carbon nanotube from the reactive function Y.

The expression "Y is derived from a reactive group" means that Y is a heteroatom or a functional group which has been modified by a chemical reaction generating a new covalent bond.

It is clear from the preceeding description, that —O— is derived from the reactive group —OH, —NH is derived from the reactive group —NH$_2$, —COO— is derived from the reactive group —COOH, —S— is derived from the reactive group —SH, —CH= and —CH$_2$— are derived from the reactive group —CHO, —CC$_k$H$_{2k+1}$ and —CHC$_k$H$_{2k+1}$— are derived from the reactive group: ketone, and in particular —CCH$_3$= and —CHCH$_3$— are derived from the reactive group —COCH$_3$.

As to the azide, it is a protected group.

As to the halide, the corresponding derived group can be —NH—, —O—, —S—, —COO—, or an azide.

The expression "Z is a linker group" means that Z is a chemical entity which is covalently linked to Y and allows the coupling of P, and which is resistant to the chemical reaction in the conditions of coupling for P, and which is capable of releasing P, but not of being released from Y.

According to a preferred embodiment Z refers to linker groups of the following formulae:

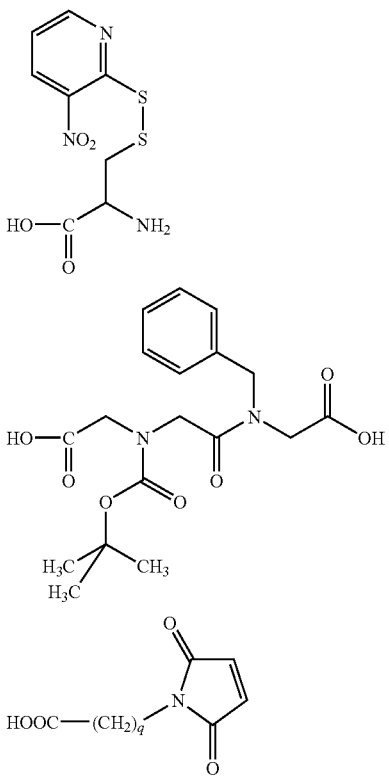

wherein q is an integer from 1 to 10;

The linker groups Z are present under varying forms depending on whether they are free, or linked to —Y— and/or linked to —P, or cleaved from —P and whether they are protected or not. The major forms of the preferred linker groups according to the invention are as follows:

free unprotected form:

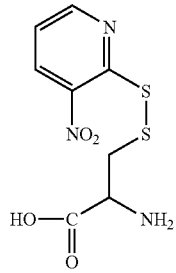

free protected form:

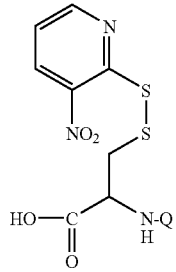

unprotected form linked to -Y-:

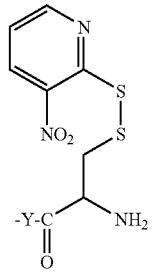

protected form linked to -Y-:

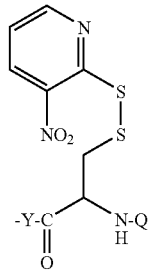

unprotected form linked to -Y- and -P:

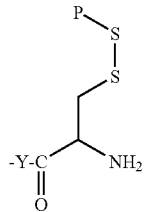

-continued
protected form linked to -Y- and -P:
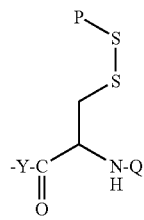
unprotected form linked to -Y- and cleaved from -P:
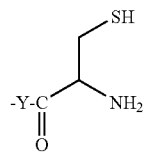
protected form linked to -Y- and cleaved from -P:
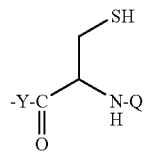
unprotected form linked to -P:
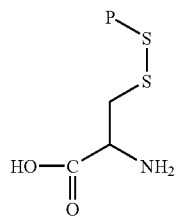
protected form linked to -P:
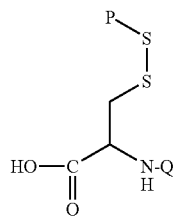
free unprotected form:
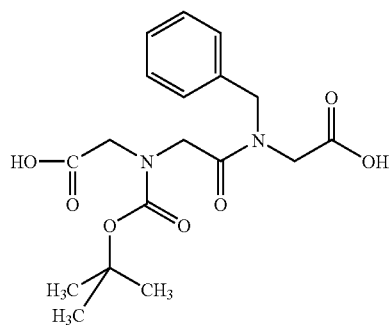
-continued
free protected form:
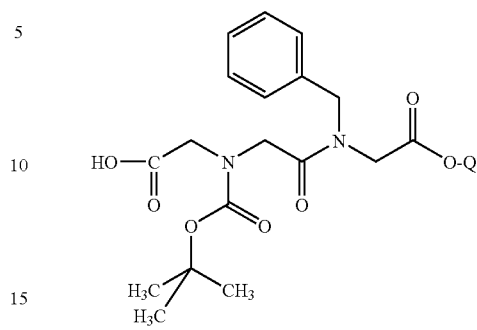
unprotected form linked to -Y-:
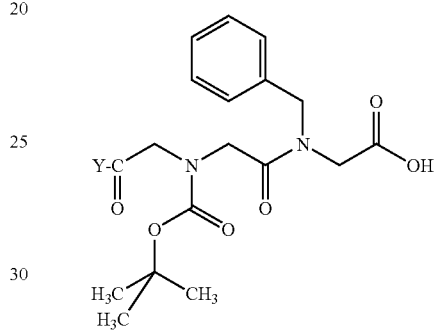
protected form linked to -Y-:
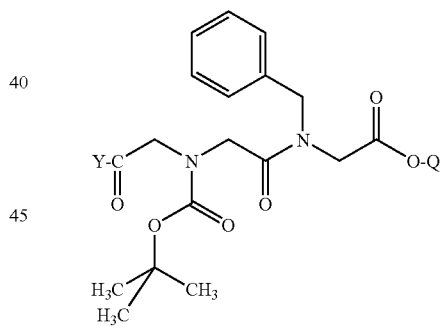
form linked to -Y- and -P-:
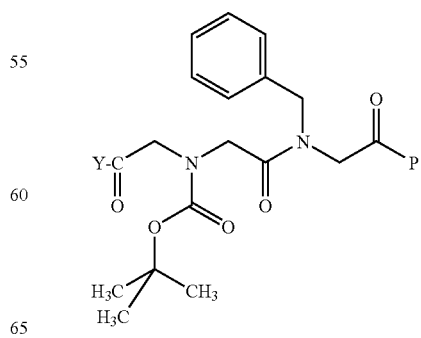

form linked to -P-:

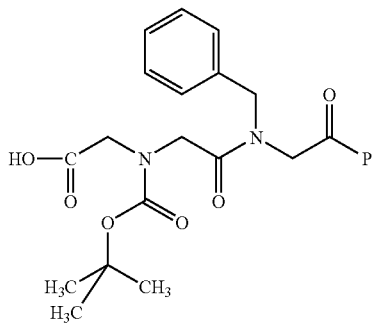

free form of maleimide:

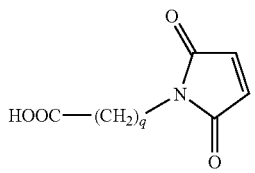

form of maleimide linked to -Y-:

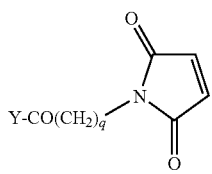

form of maleimide linked to -Y- and -P-:

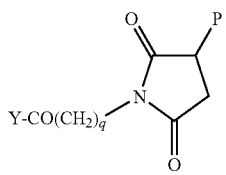

form of maleimide linked to -P:

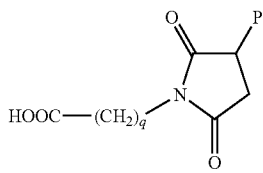

wherein q is an integer from 1 to 10, Q is a protecting group and —Y— is covalently linked to a functionalized carbon nanotube of the invention through a spacer M;

The expression "P is an effective group" means that P is a group which can confer new physical, chemical or biological properties to the carbon nanotube which carries it.

The expression "P is capable of allowing a spectroscopic detection of the carbon nanotubes" of the invention means that P is a group such as a chromophore capable of being identified by spectroscopic techniques, such as fluorescence microscopy, or nuclear magnetic resonance or FTIR (Fourier Transformed Infra-Red) spectroscopy.

The expression "active molecule liable to induce a biological effect" means that said molecule is able to modify the processes of a given biological system by establishing specific interactions with components of said biological system.

"FITC" designates fluoresceine isothiocyanate.

"DTPA" designates diethylenetriaminepentaacetic acid dianhydride.

The expression "pseudopeptide" designates a chain of amino acids of natural or non-natural origin, which contains at least one bond, the chemical nature of which is different from an amide bond.

The expression "capping group" refers to a group capable of blocking the reactive functional group Y and which can not be removed by a chemical reaction.

The expression "protecting group" refers to a group capable of temporarily blocking the reactive functional group Y and which can be subsequently removed by a chemical reaction in order to liberate the reactive function Y for further modifications.

The nature of Z, when P is present, gives rise to two types of carbon nanotubes, those wherein P can be released or those wherein P cannot be released.

If P is present, the expression "release of P", means that in the group -M-Y-Z-P, a cleavage might occur at the right extremity of the Z group.

When the cleavage takes place at this extremity of the Z group, then P is released.

When Z represents one of the two following molecules, and when P is present, P can be released because a cleavage can take place on the bond contiguous to the S atom, in the case of the left molecule, or P can be released from the right —COO— extremity, in the case of the right molecule.

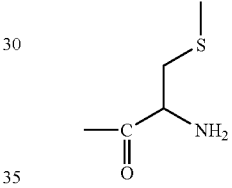

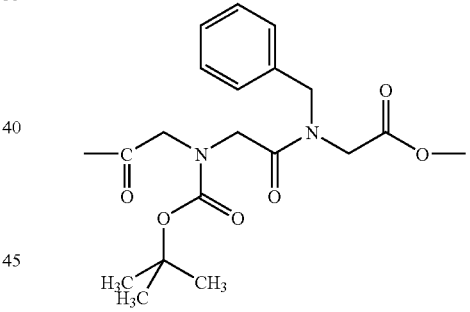

When Z represents the following molecule, and when P is present, P cannot be released, in particular under physiological conditions, such as those found in the serum, or conditions reproducing physiological conditions such as NaCl 0.15 M at pH 7.4, or PBS at pH 7.4.

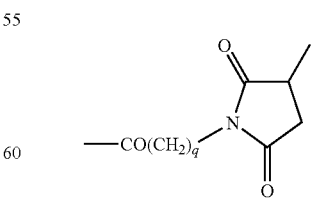

According to another embodiment of the invention, the functionalized nanotubes of the invention are such that there is generally no cleavage between M and Y, and between Y and Z.

In a further embodiment of the of the above defined complex, X represents two different substituted pyrrolidine rings, provided that at least one of said pyrrolidine rings is substituted by at least one charge-carrying group, of the following general formula (I'):

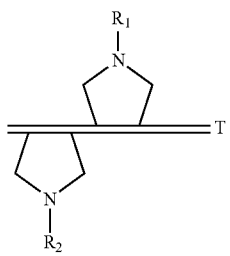

wherein T represents a carbon nanotube, $R_1$ and $R_2$ are different and represent, independently from each other, —H or a group of formula -M-Y—$(Z)_a$—$(P)_b$, M, Y, Z, P, a and b, being as defined above, at least one of $R_1$ and $R_2$ comprising a charge carrying group.

In a preferred embodiment of the complex defined above, the complex is characterized in that it corresponds to the following general formula (II):

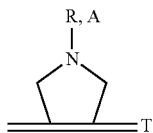

wherein T represents a carbon nanotube, A represents a charged molecule, and R represents a group of formula -M-W, and:

M is a spacer group from about 1 to about 100 atoms, such as a group selected from the list comprising —$(CH_2)_r$— or —$(CH_2$—$CH_2$—$O)_r$—$CH_2$—$CH_2$—, wherein r is an integer from 1 to 20;

W is a charge-carrying group from about 1 to about 400 atoms, such as —$NH_3^+$ or —$COO^-$.

In a particularly preferred embodiment of the complex defined above, the complex is characterized in that it corresponds to the following general formula (II'):

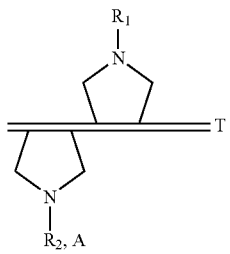

wherein T represents a carbon nanotube, A represents a charged molecule, and $R_1$ represents a group of formula -M-Y—$(Z)_a$—$(P)_b$, M, Y, Z, P, a and b, being as defined above, in particular $R_1$ represents a group carrying a fluorophore and, $R_2$ represents a group of formula -M-W, W being a charge-carrying group from about 1 to about 400 atoms, such as —$NH_3^+$ or —$COO^-$.

Several procedures are available for the functionalization of a carbon nanotube with two different pyrrolidine rings (a bisfunctionalized carbon nanotube). Details are reported in examples 1A, 1B, 1C.

In another particularly preferred embodiment of the invention, the charged molecule is selected from the group comprising:

nucleic acids, such as RNA or DNA, in particular plasmids or artificial chromosomes, comprising from 2 to 106 nucleotides, peptides, polypeptides or proteins, comprising from 2 to 5000, preferably from 50 to 5000, amino acids, carbohydrates, in particular positively charged carbohydrates, such as glucosamine or chitosane, radionucleides, and cytotoxic molecules.

Complexes according to the invention can more particularly comprise single stranded or double stranded nucleic acids. Single stranded nucleic acids carrying complexes are particularly suited for delivering antigens DNA into cells. Double stranded DNA carrying complexes are particularly suited for transforming or transfecting cells, and double stranded RNA carrying complexes are particularly useful for delivering interference RNA into cells.

Complexes comprising radionucleides according to the invention are particularly useful for imaging or therapeutic purposes.

Complexes comprising cytotoxic molecules according to the invention are particularly useful for therapeutic purposes, in particular in the frame of cancer treatment, to destroy malignant cells.

In still another particularly preferred embodiment of the complex defined above, the complex is characterized in that it corresponds to the following formula:

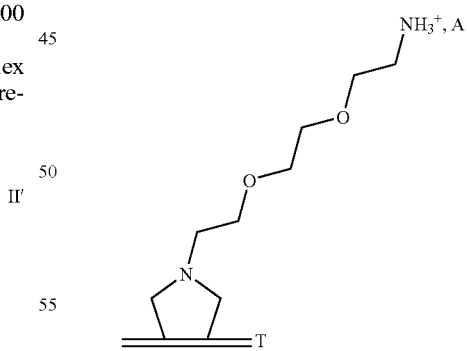

wherein T represents a carbon nanotube, and A represents a charged molecule, comprising at least one negative charge, such as DNA.

Such a complex is particularly suited for the transformation or the transfection of cells by DNA.

In another particularly preferred embodiment of the complex defined above, the complex is characterized in that it corresponds to the following formula:

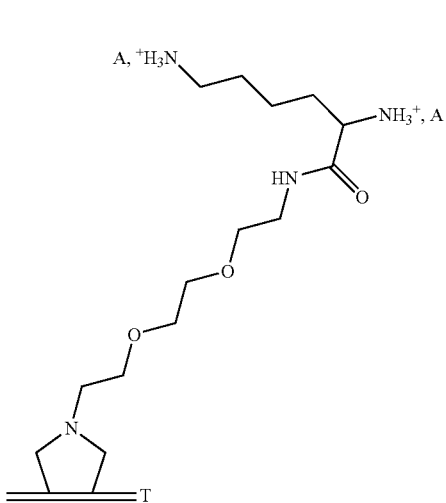

wherein T represents a carbon nanotube, and A represents a charged molecule, comprising at least one negative charge, such as DNA.

Such a complex is also particularly suited for the transformation or the transfection of cells by DNA.

In still another particularly preferred embodiment of the invention, the complex is characterized in that it corresponds to the following formula:

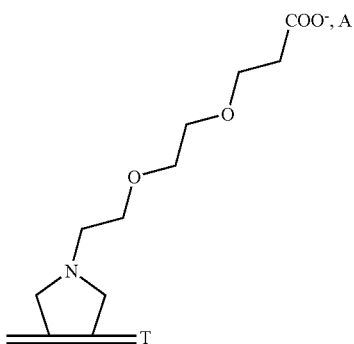

wherein T represents a carbon nanotube, and A represents a charged molecule comprising at least one positive charge.

Such a carbon nanotube can be in particular used to carry positively charged molecules, such as positively charged proteins for instance.

In yet another particularly preferred embodiment of the invention, the complex is characterized in that it corresponds to the following formula:

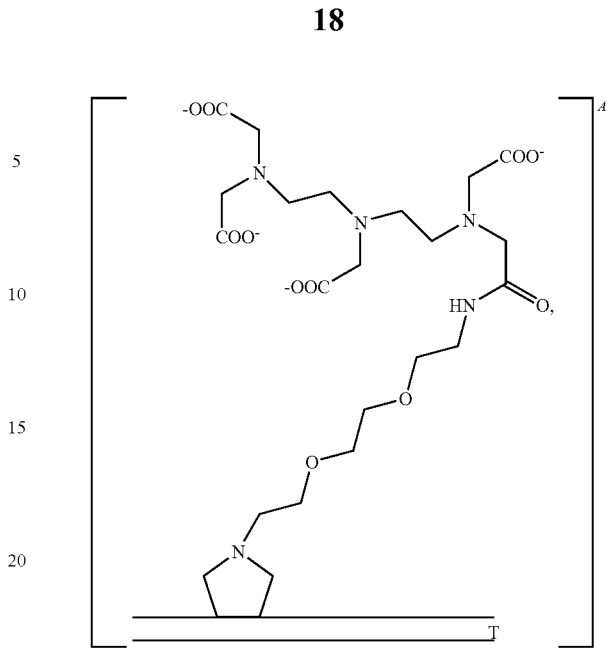

wherein T represents a carbon nanotube, and A represents a charged molecule comprising at least one positive charge.

Such a DTPA substituted carbon nanotube can be in particular used to carry positively charged molecules, such as positively charged proteins for instance.

The present invention also relates to the use of a complex as defined above, for the delivery of the charged molecules into cells.

Accordingly, the complex can be administered to an individual and remain under its associated form during while it is transported in the individual's transport fluids, such as blood or lymph, and during its passage through cellular membranes, then, once it has penetrated into a cell, it can dissociate to liberate the charged molecules.

The complexes according to the invention can penetrate into cells by energy-independent mechanisms. In particular their penetration can be endocytosis- and phagocytosis-independent.

The present invention further relates to a pharmaceutical composition comprising as active substance a complex such as defined above, in association with an acceptable pharmaceutical carrier.

Such pharmaceutical compositions are useful for the manufacture of genetic medicines or immunotherapeutic and vaccination pharmaceuticals. More particularly, they are useful for the delivery of therapeutic proteins into cells, or in the frame of gene therapy or DNA vaccine, to deliver therapeutic or prophylactic nucleic acid fragments into cells.

DESCRIPTION OF THE FIGURES

FIG. 1 represents the molecular structures of ammonium functionalized single-walled carbon nanotubes (SWNT-$NH_3^+$ 1), ammonium functionalized multi-walled carbon nanotubes (MWNT-$NH_3^+$ 2), and lysine functionalized single-walled carbon nanotubes (SWNT-Lys-$NH_3^+$ 3).

FIGS. 2A-2D represent ultra-thin transverse section of HeLa cells treated with amino $f$-MWNT (MWNT-$NH_3^+$ 2) (conc. 2.5 mg/ml). After incubation, the cell were fixed, stained, dehydrated and embedded into Epon® 812 resin.

Ultrathin layers (90 nm thickness) were cut with ultramicrotome. FIG. 2A (A) represents the entire cell, FIG. 2B (B) and FIG. 2C(C) two subsequent magnifications. FIG. 2D (D) represents a multi-walled carbon nanotube crossing the cell membrane. Dotted white arrow indicates chromatin; dashed white arrow indicates a mitochondrium; thin white arrow indicates Golgi's complex; medium arrow indicates nuclear membrane; thick white arrow indicates a vacuolum.

FIGS. 3A-3F represent the flow cytometry analysis of HeLa cells in the absence of carbon nanotubes (FIG. 3A) and incubated with SWNT-$NH_3^+$ 1 at 0.01 mg/ml (FIG. 3B), 0.1 mg/ml (FIG. 3C), 1.0 mg/ml (FIG. 3D), 10 mg/ml concentration (FIG. 3E), respectively. After incubation for 6 h and washings, the cells were analyzed. For each independent experiment, cells were stained with propidium iodide (relative intensity on Y-axis) and annexinV-APC (relative intensity on X-axis). The internalisation of functionalized carbon nanotubes was monitored by FACS technique, analysing the cellular relative content of fluorescein probe covalently linked to the SWNT (FIG. 3F). The continuous black line represents the cellular population analyzed after the treatment with SWNT-FITC at 3.0 mg/ml 12 concentration and the grey region before the treatment. More than 95% of cells have internalized the fluorescent conjugate.

FIG. 4 represents the delivery and expression of plasmid DNA by SWNT-$NH_3^+$ 1. Levels of marker gene (β-Gal) expression in relative light units per mg of total protein in CHO cells. Different (SWNT-$NH_3^+$:DNA) charge ratios were tested for three different incubation timepoints. Toxicity manifested as cell detachment and death was not observed throughout this study. SWNT-$NH_3^+$ 1 and plasmid DNA are denoted in the figure as Cnt and D, respectively.

FIGS. 5A-5C represent the expression of Luciferase in liver (FIG. 5A), lung (FIG. 5B) and spleen (FIG. 5C) of 8-10 week old male BALB/c mice.

Three animals per group were administered with 50 μg of plasmid DNA (pEGFP-Luc, Clontech) alone or pre-complexed with 600 μg of SWNT-$NH_3^+$ 1 in 0.9% (w/w) NaCl aqueous buffer following the rapid hydrodynamic injection protocol (Lecocq et al, Journal of Gene Medicine, 5(2):142-156, 2003). Tissues were collected 16 hours post-administration and Luciferase expression was assayed using the Tropix LucScreen Assay kit and a Berthold 9507 luminometer.

Figure 6A:
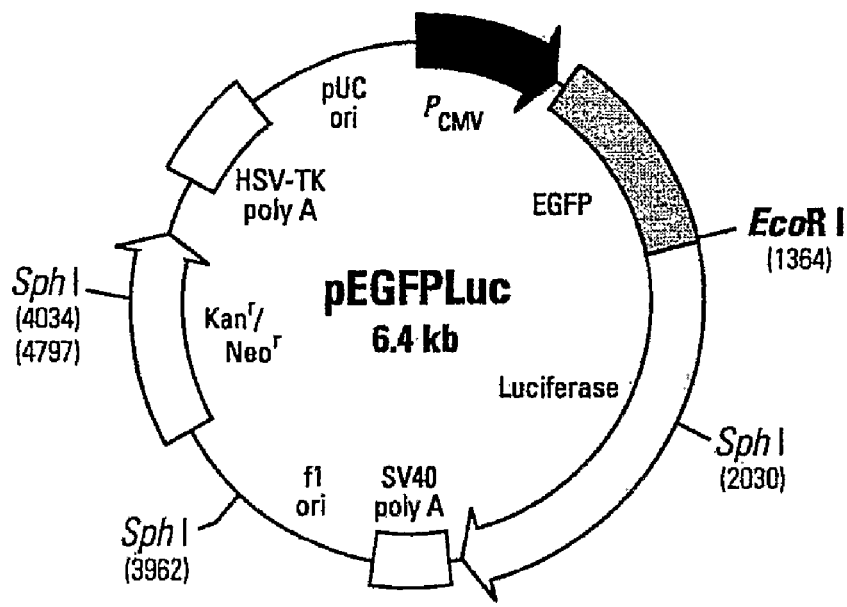
Figure 6B:
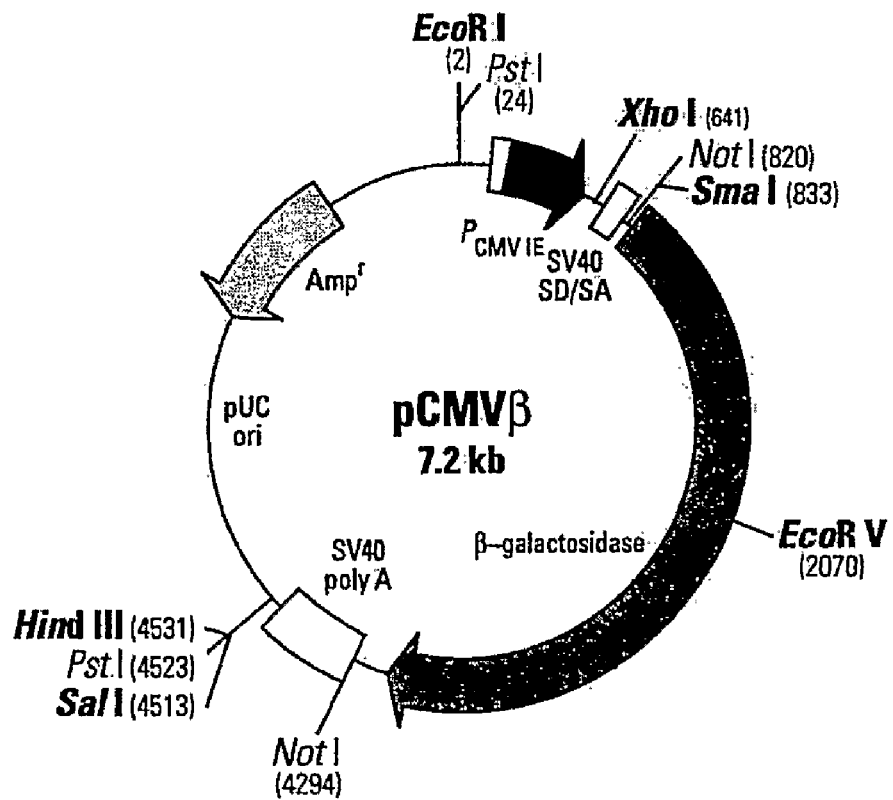

FIG. 6A and FIG. 6B

FIG. 6A represents a schematic restriction map of plasmid pEGFPLuc and FIG. 6B represents a schematic restriction map of plasmid pCMVβ.

FIG. 7

Figure 7:
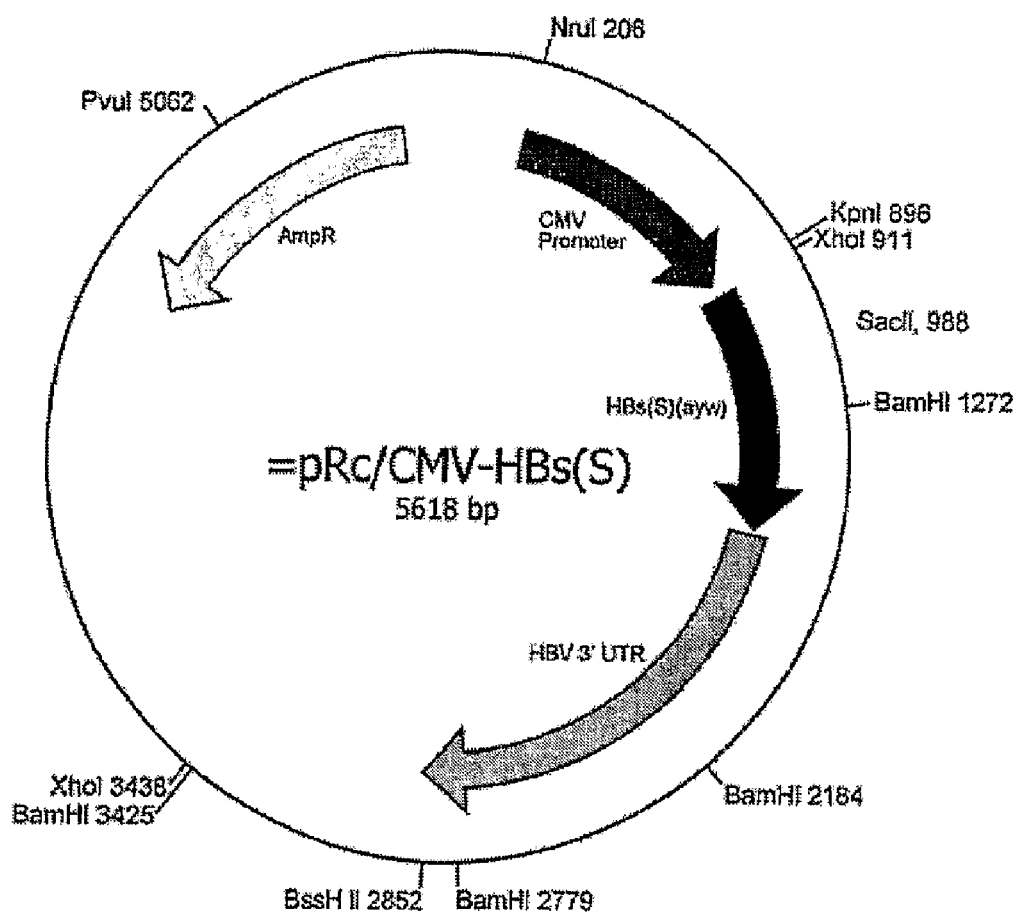

FIG. 7 represents a schematic restriction map of plasmid pRc/CMV-HBs(S).

FIG. 8A, FIG. 8B, FIG. 8C, FIG. 8D, FIG. 8E and FIG. 8F

FIGS. 8A to 8F represent SEM images of carbon nanotube:DNA complexes formed at a 6:1 charge ratio for MWNT-$NH_3^+$:DNA (FIGS. 8A-8C) and SWNT-$NH_3^+$:DNA (FIGS. 8D-8F).

FIG. 9

Figure 9:
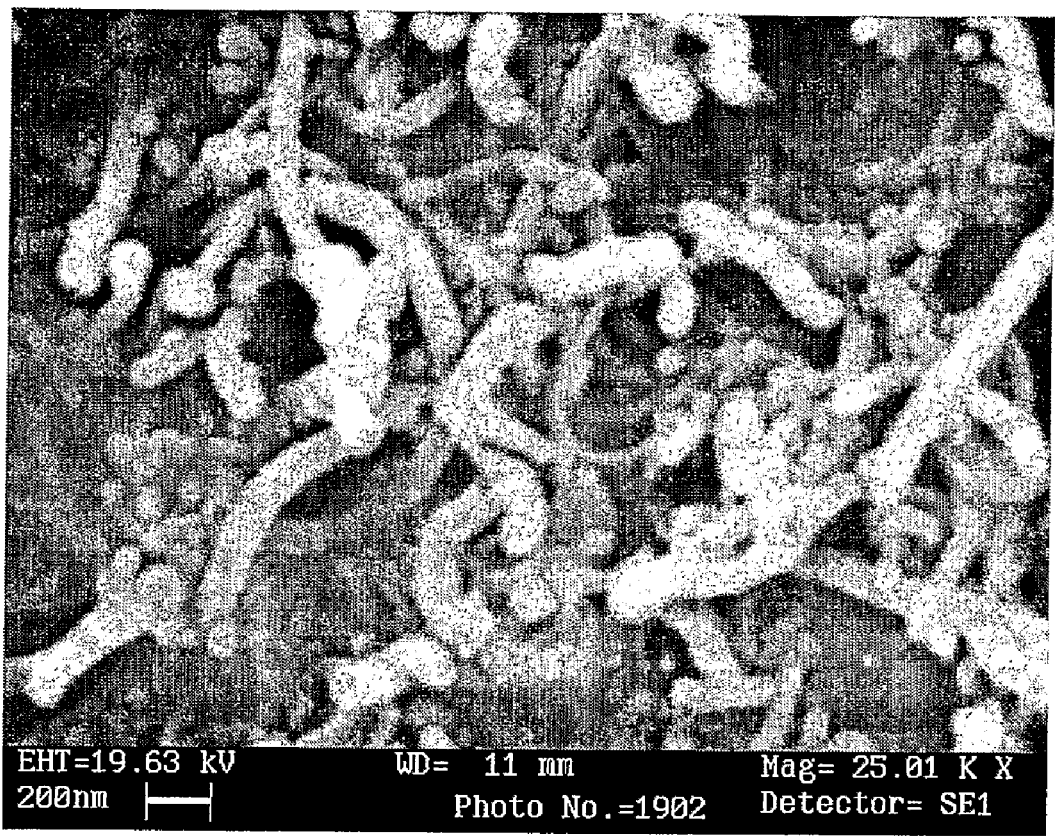

FIG. 9 represents a SEM image of a sensor chip functionalized with MWNT-$NH_3^+$ 2.

FIG. 10

Figure 10:
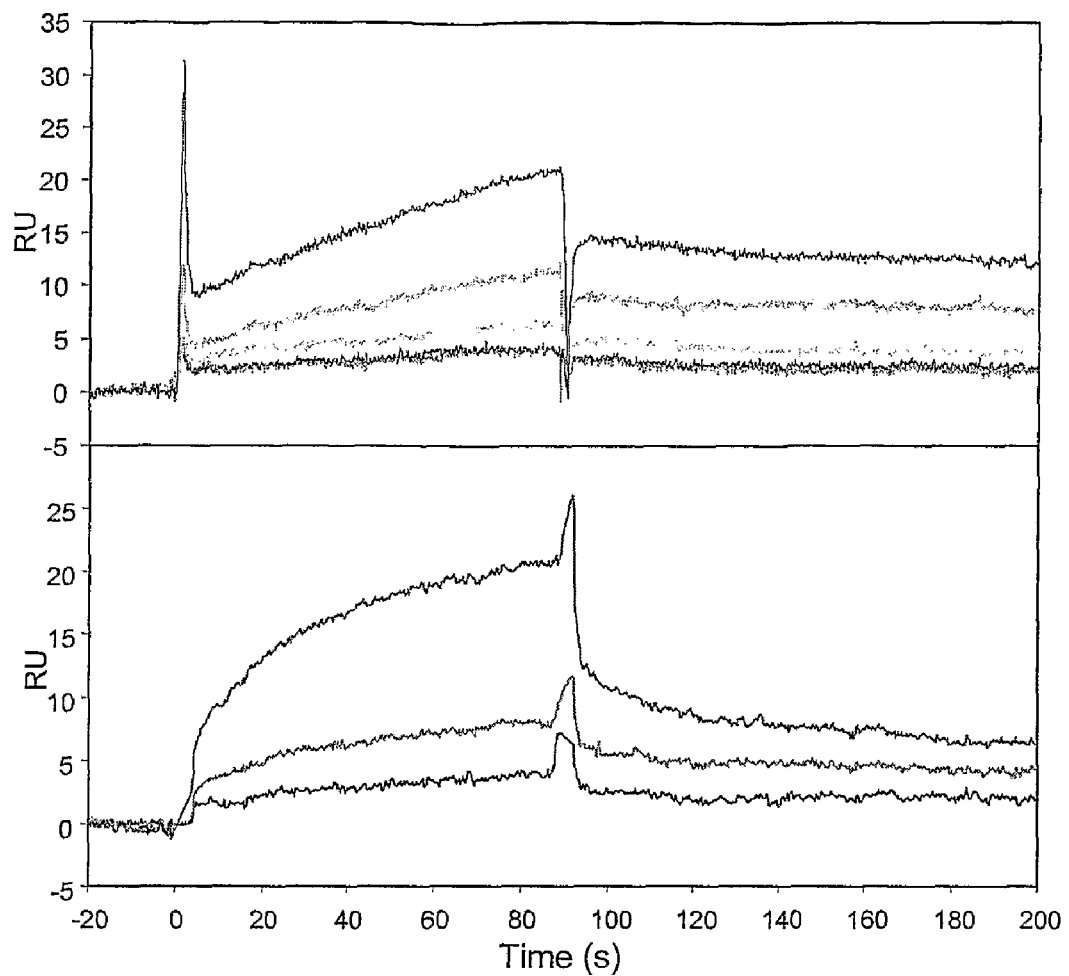

FIG. 10 represents sensorgrams of the interaction of the plasmid DNA with ƒ-CNT. Top: sensorgrams of the binding of plasmid to SWNT-Lys-$NH_3^+$ 3 by increasing the concentration of the plasmid at each run [6.3 μg/ml, 12.6 μg/ml, 25.2 μg/ml, 50 μg/ml, 100 μg/ml going from the lowest to the highest curve]. Bottom: sensorgrams of the binding of plasmid DNA to MWNT-$NH_3^+$ 2 by increasing the concentration of the plasmid at each run [25.2 μg/ml, 50 μg/ml, 100 μg/ml going from the lowest to the highest curve].

Figure 11:
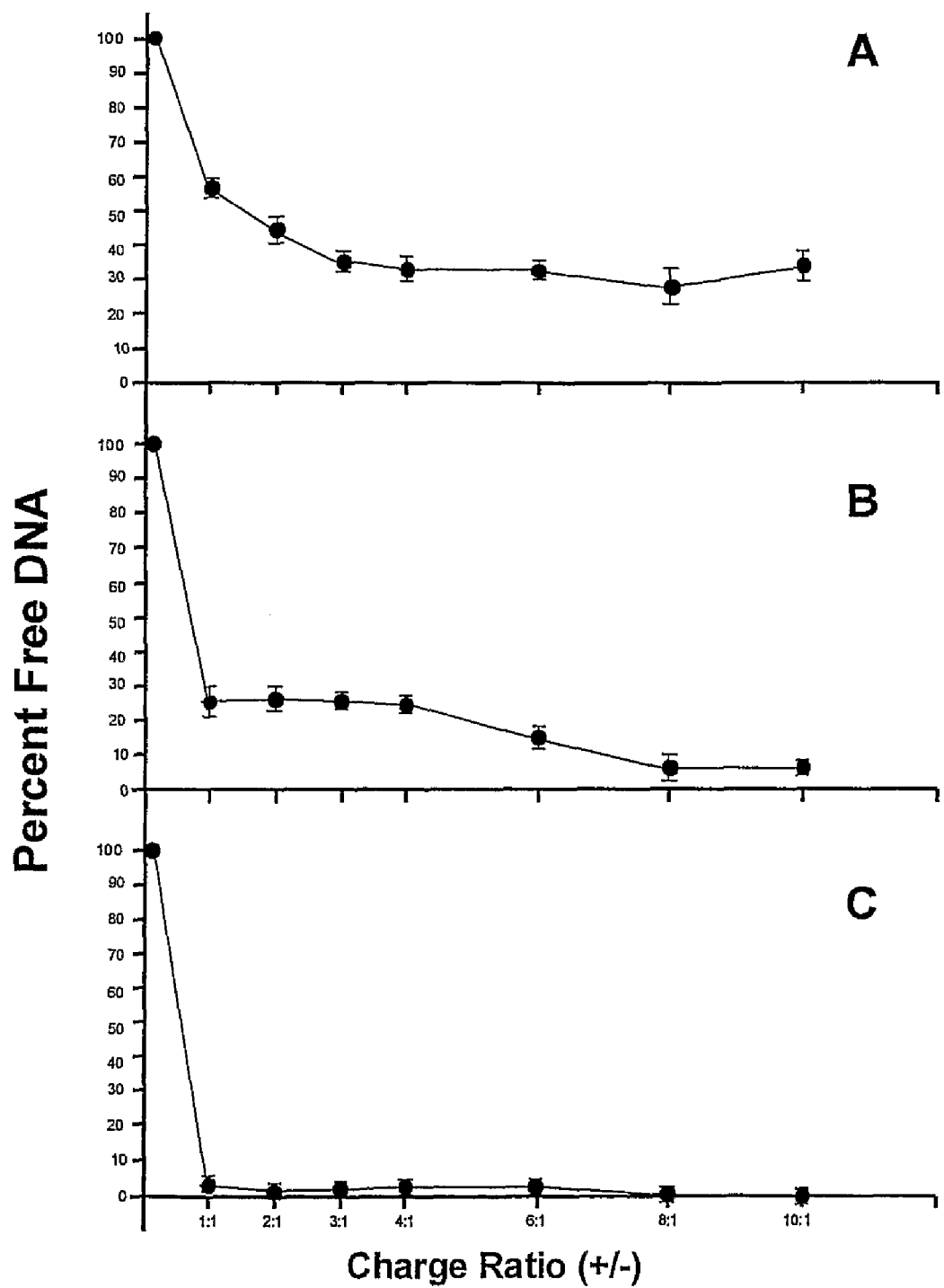

FIG. 11A, FIG. 11B and FIG. 11C

FIGS. 11A to 11C represent DNA condensation following complexation with functionalized carbon nanotubes. Condensation of 2.5 μg/ml DNA complexed to ƒ-CNT at various charge ratios expressed as percent of PicoGreen fluorescence of 2.5 μg/ml free DNA for SWNT-$NH_3^+$:DNA (FIG. 11A), SWNT-Lys-$NH_3^+$:DNA (FIG. 11B) and MWNT-$NH_3^+$:DNA (FIG. 11C).

Figure 12:
Figure 12:
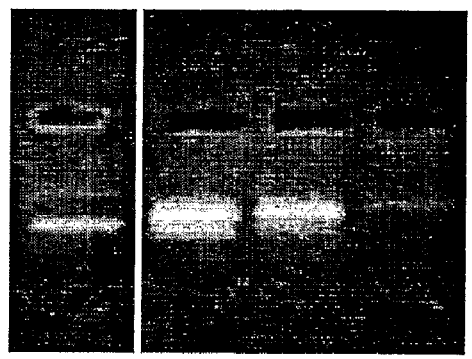
Figure 12:
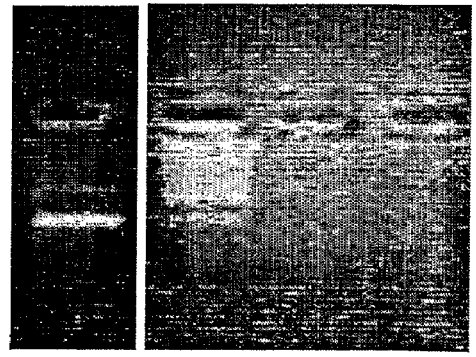

FIG. 12A, FIG. 12B and FIG. 12C

FIGS. 12A-12C represent the electrophoretic motility of ƒ-CNT-DNA complexes. In all panels, lane 1 represents 0.2 μg free DNA. All other lanes contain ƒ-CNT complexed to 0.2 μg DNA at various +/– charge ratios: lane 2, 1:1. lane 3, 6:1. lane 4, 10:1 for SWNT-$NH_3^+$:DNA (FIG. 12A), SWNT-Lys-$NH_3^+$:DNA (FIG. 12B) and MWNT-$NH_3^+$:DNA (FIG. 12C). OC=Open Circular. SC=Supercoiled.

Figure 13:
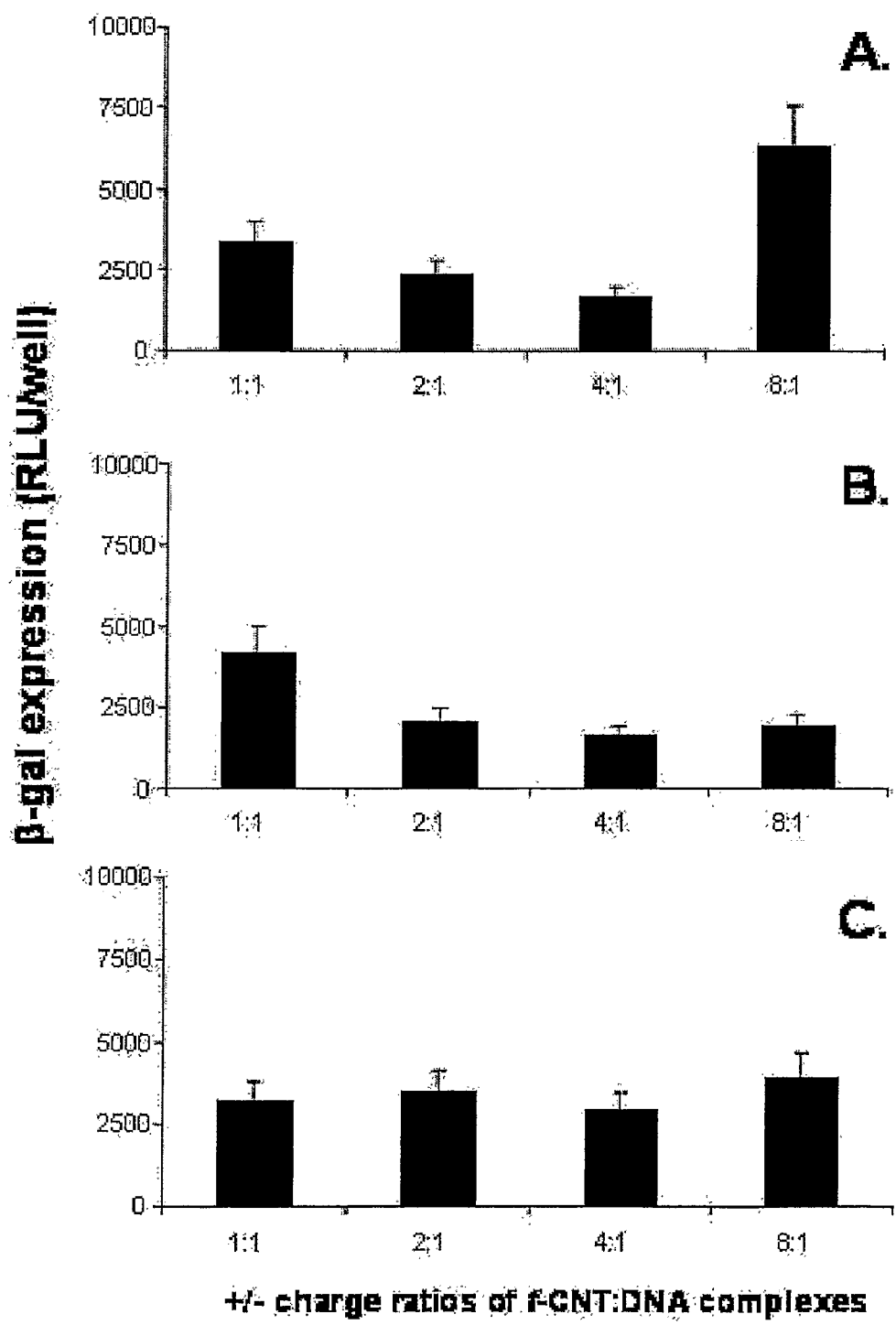

FIG. 13A, FIG. 13B and FIG. 13C

FIGS. 13A to 13B represent the expression of β-gal marker gene in human lung carcinoma cells (A549) following gene delivery with ƒ-CNT:pDNA complexes at various charge ratios; SWNT-$NH_3^+$:DNA (FIG. 13A); SWNT-Lys-$NH_3^+$:DNA (FIG. 13B), MWNT-$NH_3^+$:DNA (FIG. 13C) (gene expression levels shown above DNA control in the absence of CNT using luminometry assay)

EXAMPLES

Example 1

Figure 1:
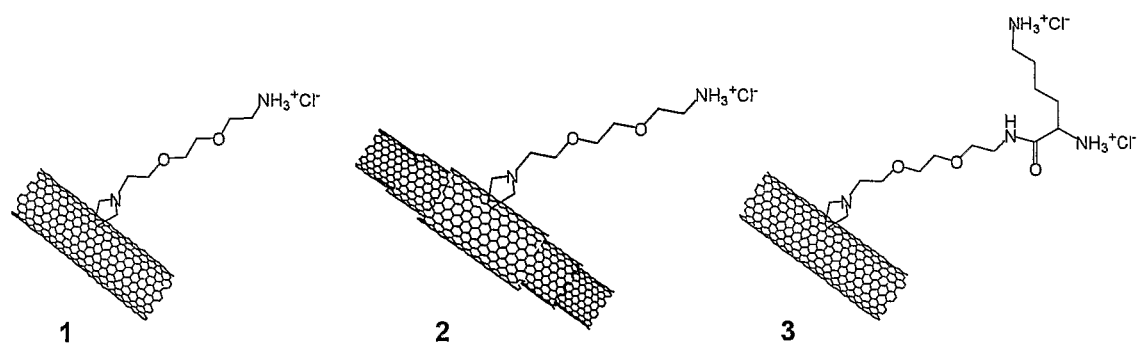
FIG. 1

Carbon nanotubes have been covalently modified using the method based on the 1,3-dipolar cycloaddition of azomethine ylides (Georgakilas et al. (2202) *J. Am. Chem. Soc.* 124:760-761). Both single-walled and multi-walled carbon nanotubes (SWNT and MWNT) have been functionalized with a pyrrolidine ring bearing on the nitrogen a free amino terminal triethylene glycol moiety (FIG. 1). The amount of functional (ƒ) groups around the carbon nanotubes was calculated at about 0.55 and 0.90 mmol/g for the ƒ-SWNT and the ƒ-MWNT, respectively. SWNT functionalized with the lysine were prepared as described by Pantarotto et al Chem. Biol. 2003, 10, 961-966, starting from SWNT-$NH_3^+$ 1. The amount of amino functions around the tubes was calculated at about 0.92 mmol/g. The positive charge distribution renders the material highly soluble in aqueous solutions.

For the formation of ƒ-SWNT:DNA complexes, amino-functionalized single-walled carbon nanotubes were hydrated in deionized water at a concentration of 6 mg/ml. Plasmid DNA, pEGFP-Luc (FIG. 6A) or pCMVβ (FIG. 6B), both from Clontech, was hydrated in deionized water at a concentration of 1 mg/ml. Aliquots were stored frozen at −20° C. until needed. For in vitro studies, the appropriate volume of nanotubes was diluted to a total volume of 300 μl in Optimem. 3 μg of pCMVβ was added to a separate tube containing 300 μl of Optimem. The diluted nanotubes were then added by drop-wise addition to the DNA, and the mixture was pipetted briefly. Complexes were allowed to form for 10 minutes prior to use. This process was repeated for each charge ratio tested. For in vivo studies, 600 μg of nanotubes was diluted in 750 μl of 0.9% NaCl. 50 μg of pEGFP-Luc, diluted in 750 μl of 0.9% NaCl, was added by drop-wise addition to the nanotubes, and the mixture was pipetted briefly. This process was repeated three times, yielding a nanotube to DNA charge ratio of 2:1 in all cases.

Example 1A

Preparation of a Bis-Functionalized Carbon Nanotube

A first procedure can proceed as described in the following reaction scheme:

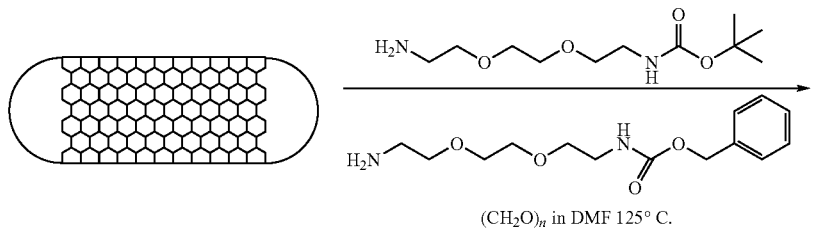

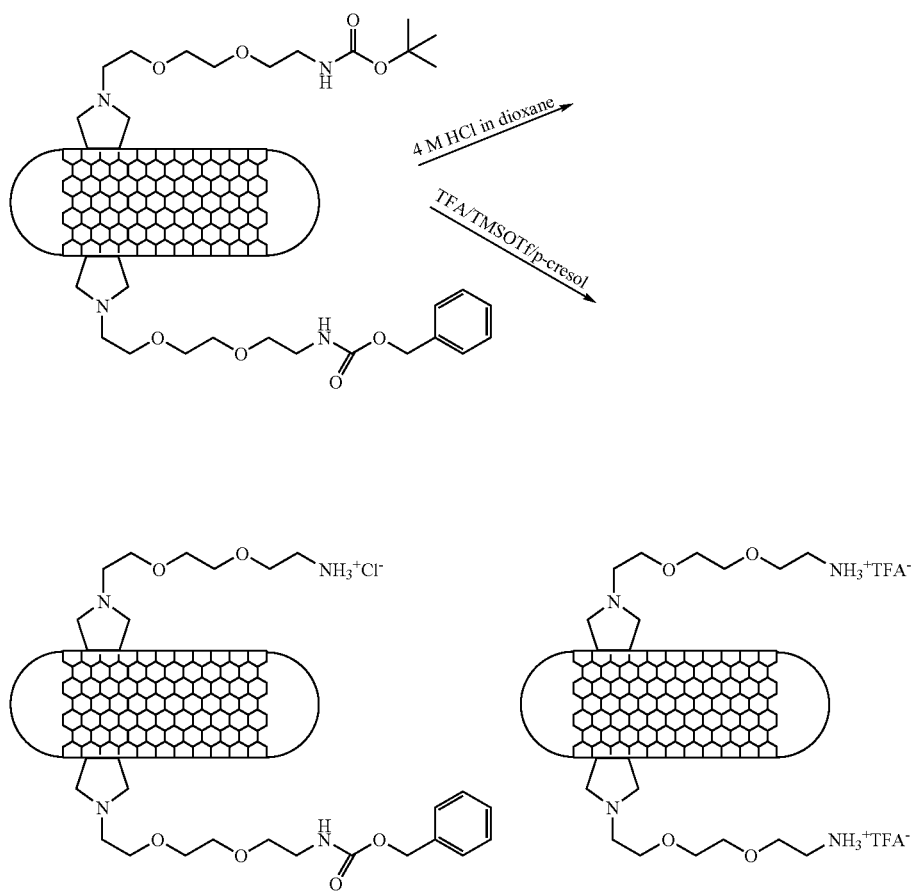

Briefly, carbon nanotubes (100 mg) and paraformaldehyde (3×150 mg every 24 hours) are suspended in 100 ml of DMF. About 150 mg of Boc-NH—($CH_2CH_2O)_2$—$CH_2CH_2$—$NHCH_2COOH$ and 167 mg Z-NH—($CH_2CH_2O)_2$—$CH_2CH_2$—$NHCH_2COOH$ (1:1 molar ratio) are added and the reaction is heated at 125° C. for 72 hours. The heating is stopped and the organic phase is separated from the unreacted material by centrifugation and filtration through a 0.22 μm PTFE filter. The filtrate is evaporated and the brown residue is dissolved in DCM, washed once with water and dried over $Na_2SO_4$. The solvent is evaporated and the product is reprecipitated several times from methanol/diethyl ether. The functionalized carbon nanotubes are characterized by TEM and $^1$H-NMR.

Example 1B

Preparation of a Bis-Functionalized Carbon Nanotube

A second procedure can proceed as described in the following reaction scheme:

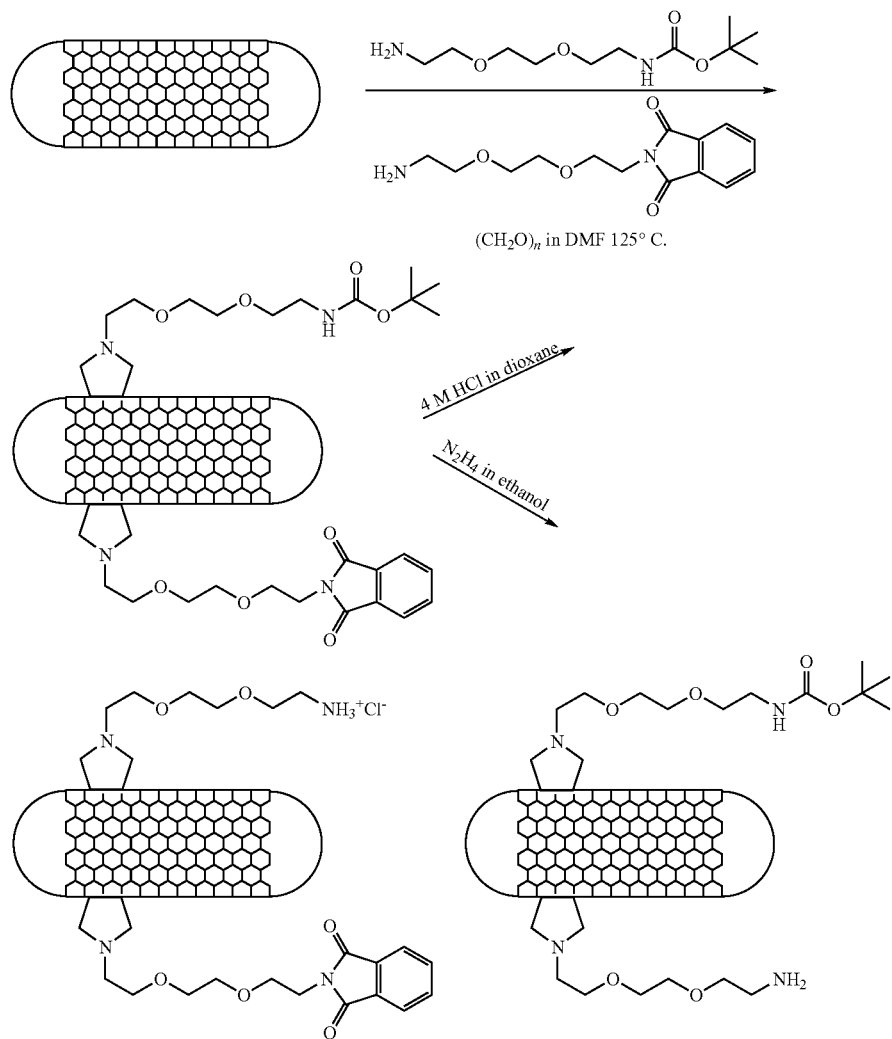

Briefly, carbon nanotubes (100 mg) and paraformaldehyde (3×150 mg every 24 hours) are suspended in 100 ml of DMF. About 150 mg of Boc-NH—(CH$_2$CH$_2$O)$_2$—CH$_2$CH$_2$—NHCH$_2$COOH and 165 mg Pht-NH—(CH$_2$CH$_2$O)$_2$—CH$_2$CH$_2$—NHCH$_2$COOH (1:1 molar ratio) are added and the reaction is heated at 125° C. for 72 hours. The heating is stopped and the organic phase is separated from the unreacted material by centrifugation and filtration through a 0.22 μm PTFE filter. The filtrate is evaporated and the brown residue is dissolved in DCM, washed once with water and dried over Na$_2$SO$_4$. The solvent is evaporated and the product is reprecipitated several times from methanol/diethyl ether. The functionalized carbon nanotubes are characterized by TEM and $^1$H-NMR.

The cleavage of the Boc protecting group for the first and the second procedure can be performed as described hereafter. A solution of HCl 4 M in dioxane is added to bis-functionalized carbon nanotubes (5 mg) and the mixture is stirred for 5 hours at room temperature. The solvent is removed under reduced pressure and the product is reprecipitated several times from methanol/diethyl ether. The functionalized carbon nanotubes are characterized by TEM and $^1$H-NMR. Quantitative Kaiser test: 0.35 mmol/g of free NH$_2$.

In the first procedure (EXAMPLE 1A), a simultaneous cleavage of Z and Boc protecting group can be done according to the following protocol. A solution (400 μl) of TFA/TMSOTf/p-cresol (325:87:42.5, μl/μl/mg) is added to bis-functionalized carbon nanotubes (5 mg) and the mixture is stirred for 12 hours at room temperature. The product is directly precipitated in diethyl ether and washed several times by reprecipitation from methanol/diethyl ether. The functionalized carbon nanotubes are characterized by TEM and $^1$H-NMR. (TMSOTf, trimethylsilyltrifluoromethanesulfonate). Quantitative Kaiser test: 0.70 mmol/g of free NH$_2$.

The Z/Boc strategy is not completely orthogonal. Indeed, it is not possible to remove the Z group without affecting the Boc group that protects part of the amino functions on the carbon nanotubes side walls.

In the second procedure (EXAMPLE 1B), the cleavage of the phthalimide protecting group is performed as follows. Hydrazine (36.5 μl, 752 μmol) in ethanol (10 ml) is added to bis-functionalized carbon nanotubes (9.4 mg) and the mixture is stirred for 16 hours at room temperature under argon. The solvent is removed, methanol is added and the solution is centrifuged to eliminate phthalhydrazide. The product is reprecipitated several times from methanol/diethyl ether. The functionalized carbon nanotubes are characterized by TEM and $^1$H-NMR. Quantitative Kaiser test: 0.6 mmol/g of $NH_2$.

Once selectively deprotected, the reactive groups corresponding to the respective pyrrolidine rings can be substituted according to methods well known to the man skilled in the art.

Example 1C

Preparation of a Bis-Functionalized Carbon Nanotube

In a third procedure, bis-functionalized carbon nanotubes can be reacted with fluorescein isothiocyanate. This procedure is depicted in the following reaction scheme:

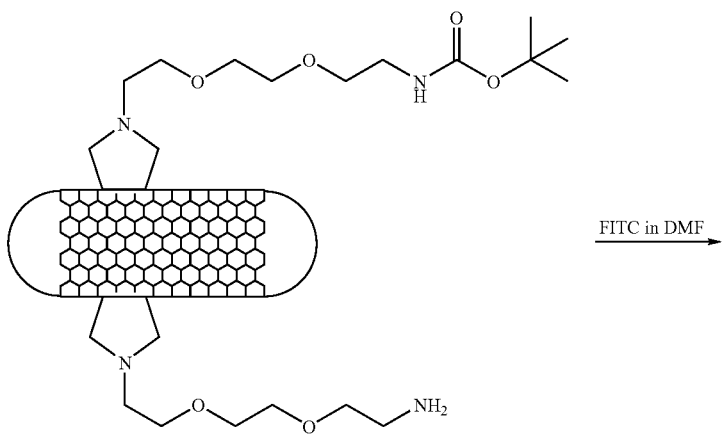

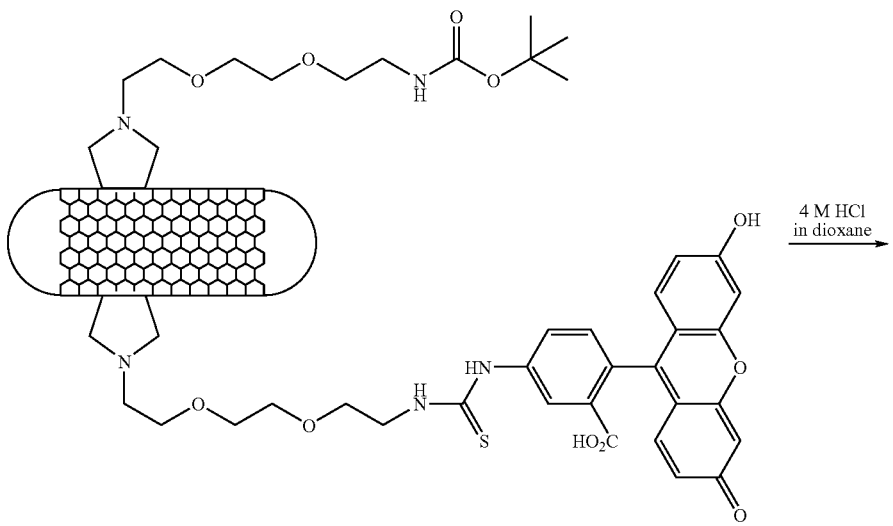

-continued

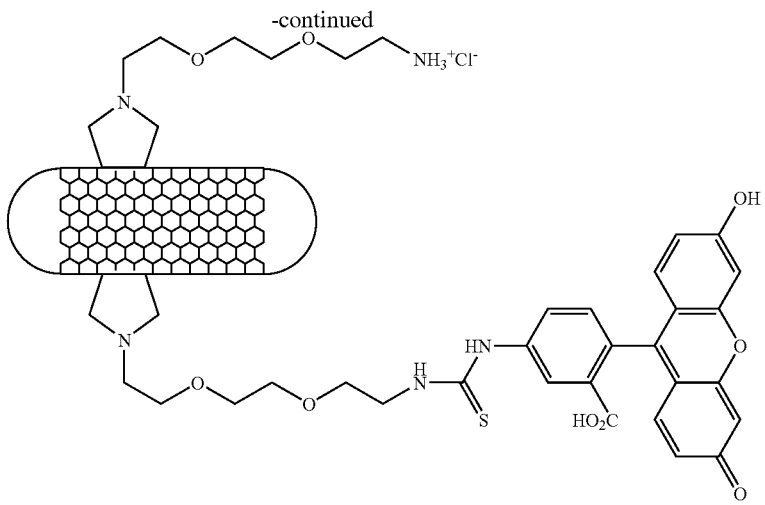

Briefly, amino functionalized carbon nanotubes (7 mg, 4.2 μmol corresponding to the amount of free $NH_2$ measured with quantitative Kaiser test) are solubilized in 200 μl of DMF. A solution of fluorescein isothiocyanate (FITC) (4.9 mg, 12.6 μmol) in 200 μl of DMF is added and the solution is stirred overnight at room temperature. The solvent is removed and the product is precipitated several times from methanol/diethyl ether. The Kaiser test is negative. The functionalized carbon nanotubes are characterized by TEM and UV-Vis.

For the third procedure, the cleavage of the Boc protecting group can be performed as follows. A solution of HCl 4 M in dioxane is added to bis-functionalized carbon nanotubes (5 mg) and the mixture is stirred for 5 hours at room temperature. The solvent is removed under reduced pressure and the product is reprecipitated several times from methanol/diethyl ether. The functionalized carbon nanotubes are characterized by TEM.

Quantitative Kaiser test: 0.35 mmol/g of $NH_2$.

Example 2

The capacity of the functionalized CNT to penetrate into the cells was studied.

Previously, the Inventors had been able to visualize carbon nanotubes interacting and being uptaken into cells upon labelling with a fluorescent probe (FITC). A different experimental approach using transmission electron microscopy (TEM) was carried out presently, in an attempt to identify the specific intracellular compartments where localization of carbon nanotubes occurred.

HeLa cells were cultured using DMEM medium at 37° C. and after growth to more than 80% confluency, amino-free $f$-SWNT and $f$-MWNT (FIG. 1) at 2.5 mg/ml concentration, were added to the cells. The nanotubes were allowed to interact with the cells for 1 h, and the cells were then washed, fixed, stained, dehydrated and embedded into Epon® 812 resin. The polymer was then cut into ultrathin layers of about 90 nm thickness using a diamond ultramicrotome, and different slices were analyzed with TEM.

More precisely, SWNT and MWNT, obtained from Carbon Nanotechnology, Inc. and Nanostructured & Amorphous Materials, Inc., respectively, were functionalized as described in Georgakilas et al. (2002) *J. Am. Chem. Soc.* 124:760-761. HeLa cells ($1.25 \times 10^5$) were cultured into a 16-wells plate using DMEM medium at 37° C. and 5% $CO_2$ until 75% of confluence. The cells were then incubated with a solution of 2.5 mg/ml of $f$-SWNT-$NH_2$ and $f$-MNT-$NH_2$ in PBS for 1 hour, washed twice with PBS and fixed for 2 hours at room temperature in 2.5% glutaraldehyde in a cacodilate buffer (sodium cacodilate 0.075 M, $MgCl_2$ 1 mM, $CaCl_2$ 1 mM, 4.5% sucrose pH 7.3). An amount of 10% v/v of a 1/10 saturated solution of picric acid in cacodilate buffer was then added into each wells and incubated overnight at 4° C. The specimen was washed three times for 15 minutes using distilled water, then treated with a 1% $OsO_4$ solution of in cacodilate buffer for 2 hours at room temperature. Cells were carefully rinsed with distilled water and post-fixed with a 2% solution of uranyl acetate in water overnight at 4° C. After several washes, the cells were dried with 70% and 90% ethanol for 10 minutes each, and twice with absolute ethanol for 20 minutes. An amount of fresh Epon® 812 resin was prepared as suggested by EMS (Electron Microscopy Sciences) technical data sheet and distributed into each well. The plate was stored into an oven at 65° C. for three days. Each resin block was then removed from the plastic support and cut. A Reichert-Jung Ultracut-E ultramicrotome with a diamond knife Ultramicrotomy® 45° was used to cut the cells embedded into the resin. A thickness value of 90 nm was chosen. Three subsequent slices were deposited onto a formvar grid and observed under an electronic transmission microscope Hitachi 600 at 75 kV. Images were taken by an AMT high sensitive camera at different level of magnification.

Figure 2A:
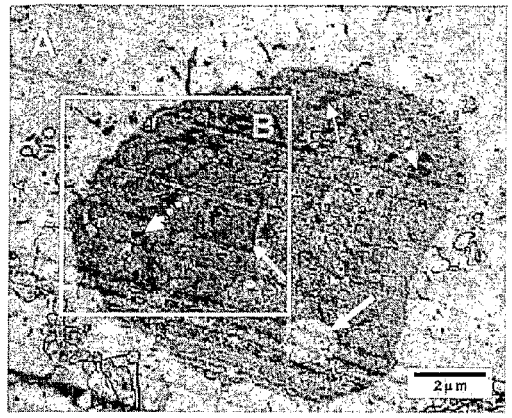
FIG. 2A, FIG. 2B, FIG. 2C and FIG. 2D
Figure 2B:
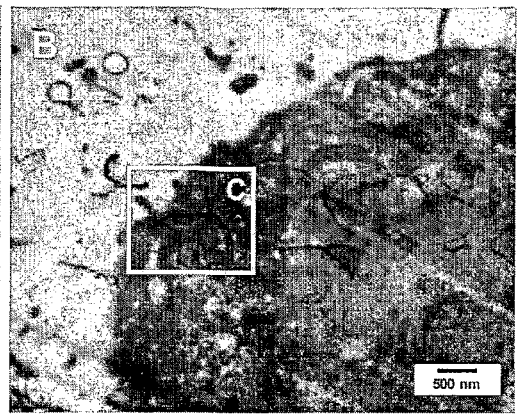
Figure 2C:
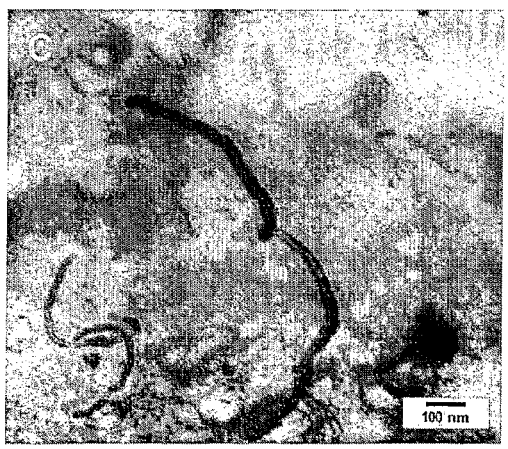
Figure 2D:
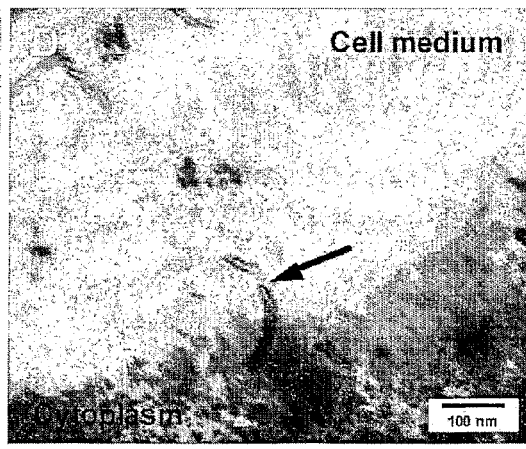

FIGS. 2A-2D represent HeLa cells incubated with the $f$-MWNT. The different cellular compartments are indicated by white arrows in FIG. 2A. Various nanotubes are clearly visible inside the cell, while subsequent magnifications (FIGS. 2B and 2C) allow a higher resolution view of the intracellular localisation of the $f$-MWNT. The same pattern of interaction with HeLa cells was found for the SWNT. Interestingly enough, some nuclear localization of the nanotubes was indeed observed consistently throughout the samples, however, more detailed studies are needed to address the intracellular trafficking, efficiency and mechanism of nuclear translocation of carbon nanotubes. Careful observation of the cell sections have also permitted observation of nanotubes during the process of crossing the plasma membrane barrier. FIG. 2D displays a $f$-MWNT during interaction with the cell membrane and uptake. The observed nanotube has a diameter of about 20 nm and a length around 200 nm. Although the type of cellular uptake is still unclear, the semi-rigid and elongated form of the tube rules out an endocytosis process. This was also confirmed by preincubation of the cells with sodium azide or 2,4-dinitrophenol, which are typical inhibitors of energy dependent cell processes, including the endocytosis mechanism. Carbon nanotubes are likely entering the cell via a passive mechanism. They seem to behave like nanoneedles, perforating the cell membrane without causing cell death. Indeed, this is in contrast with other cationic macromolecules, such as peptides and dendrimers, that in general cause destabilization of the cell membrane resulting in cell lysis (Rittner et al. (2003) Mol. Ther. 5:104-14; Boas and Heegaard (2004) Chem. Rev. Soc. 33:43-63).

The cell toxicity of the carbon nanotubes at different concentrations was then assessed by flow cytometry. For this experiment amino ƒ-SWNT or ƒ-SWNT derivatized with fluorescein isothiocianate were incubated with the cells.

Briefly, to analyze the cell viability by FACS, exponentially growing HeLa cells in DMEM supplemented with 10% (v/v) fetal calf serum, were incubated with a solution of ƒ-SWNT-$NH_2$ and ƒ-MWNT-$NH_2$ at different concentration (0.01-10 mg/ml) for 6 hours, rinsed and dissociated with trypsin for 5 minutes at 37° C., centrifuged at 1000 tr/min and washed three times with annexin V buffer solution. 100 μL of the same buffer and 0.5 μL of annexin V-FITC were added to the cells and incubated for 15 minutes in the dark. Then, 5 μL of propidium iodide staining solution (50 μg/ml) were added. The analysis was performed using a cytofluorimetry FACS-Calibur. instrument operating at 494 nm and 647 nm excitation wavelength. CellQuest® software was used for the data analysis. A minimum of 40,000 events per sample were analysed. HeLa cells were also incubated with SWNT-FITC at different concentration as described in reference 6.

Figure 3A:
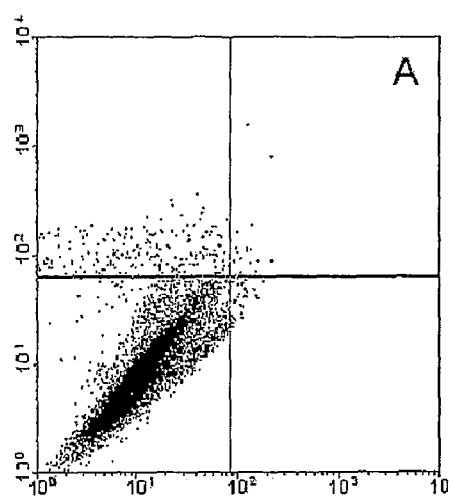
FIG. 3A, FIG. 3B, FIG. 3C, FIG. 3D, FIG. 3E and FIG. 3F
Figure 3B:
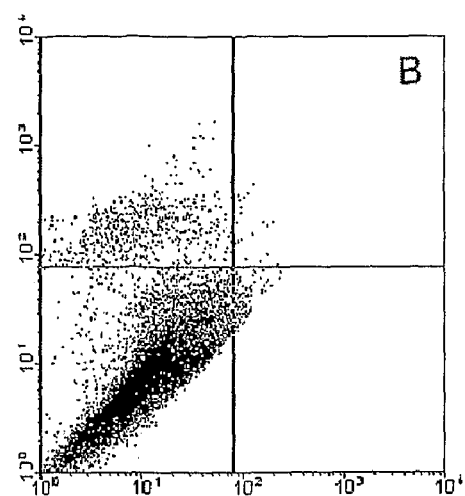
Figure 3C:
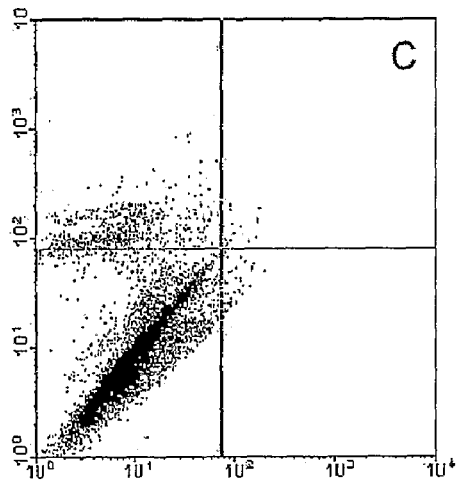
Figure 3D:
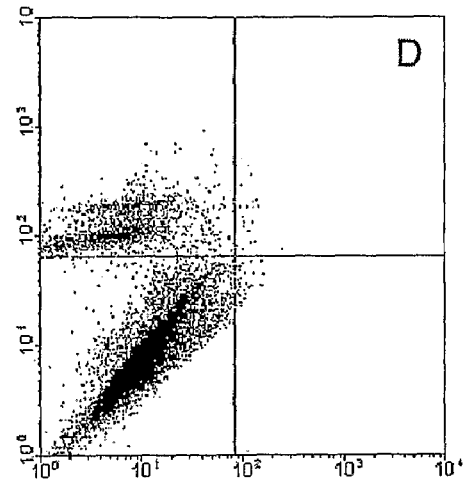
Figure 3E:
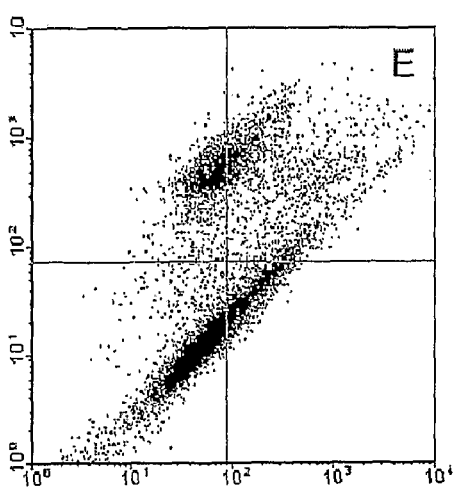
Figure 3F:
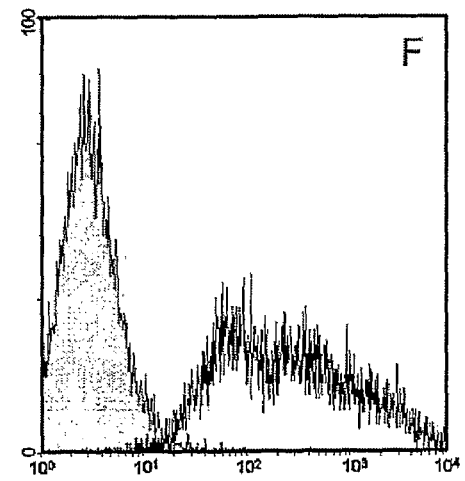

FIGS. 3A-3E represent the cell behaviour for a range of concentrations from 0.01 mg/ml to 10 mg/ml of amino ƒ-SWNT. It is evident that up to 1 mg/ml more that 80% of the cells remain alive, and only at the highest concentration of nanotubes the percentage of survival decreases to 50%. It can be observed that the amino functionalized CNT are less toxic than the previously studied SWNT-FITC. In addition, to demonstrate that the functionalized carbon nanotubes are inside the cells, the latter were incubated with 3 mg/ml of SWNT-FITC and visualized with the FACS technique (FIG. 3F). The data suggests that more than 95% of cells internalized the fluorescently labelled nanotubes, indicating a strong affinity for the cell surface and subsequent cellular internalisation. This data correlated with the electron microscopy observations shown in FIGS. 2A-2D, exhibiting the strong interaction between nanotubes and cells.

The high capacity of the amino functionalized carbon nanotubes to enter cells and reach their nuclei, was then exploited for the delivery of plasmid DNA.

CHO cells (ATCC) were grown to 90% confluency in 96 well tissue culture dishes (Corning-Costar) in F12-K media containing 10% FBS and 1% penicillin/streptomycin (all from Gibco). The culture media was removed and 50 μl of the ƒ-SWNT:DNA complexes was added to three wells for each condition. After 30, 90, or 180 minutes, the transfection media was removed and replaced with fresh culture media. As a control, three wells were transfected with 0.25 μg DNA in 50 μl of Optimem. Cells were incubated for 48 hours, then harvested. β-galactosidase activity was measured using the Tropix Galactolight Plus kit and a Berthold 9507 luminometer according to the manufacturers instructions.

Figure 4:
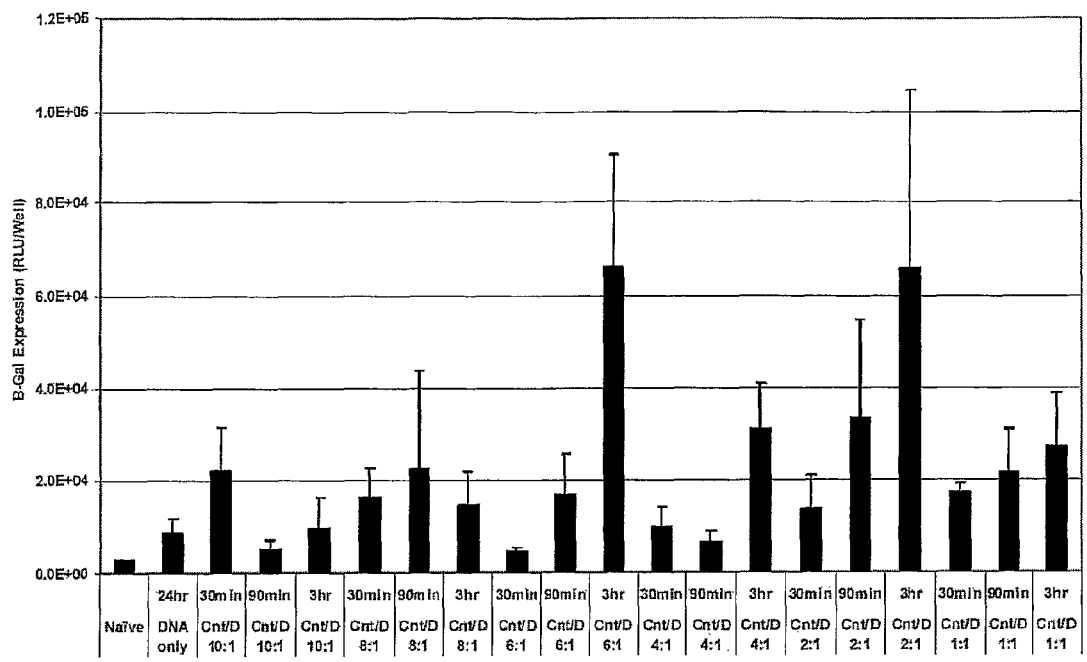
FIG. 4

FIG. 4 shows the levels of marker gene (β-galactosidase) expression in CHO cells, obtained after interaction between the nanotubes and plasmid DNA encoding the gene. In accord with other non-viral gene delivery vectors, the charge ratio between the amino groups at the SWNT surface and the phosphate groups of the DNA backbone seems to be a determinant factor of the resulting levels of gene expression. ƒ-SWNT:DNA charge ratios between 2:1 and 6:1 (+/−) offered 5 to 10 times higher levels of gene expression compared to DNA alone. Cytotoxicity was not observed throughout this study, even at 3 hours incubation time between the ƒ-SWNT:DNA and the CHO cells.

Example 3

The amino-functionalized SWNT and plasmid DNA complexes according to the invention were used for in vivo gene delivery studies.

Figure 5A:
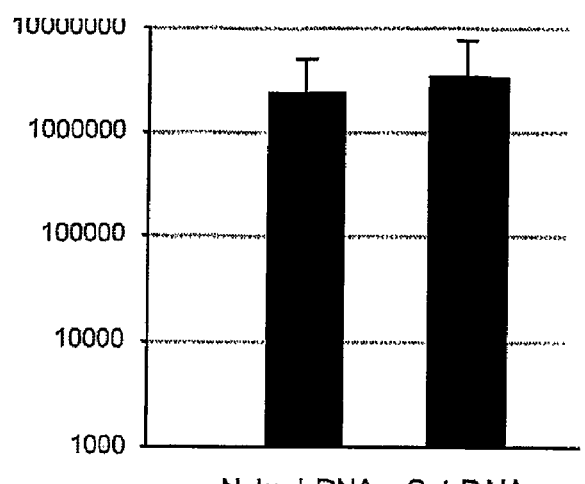
FIG. 5A, FIG. 5B and FIG. 5C
Figure 5B:
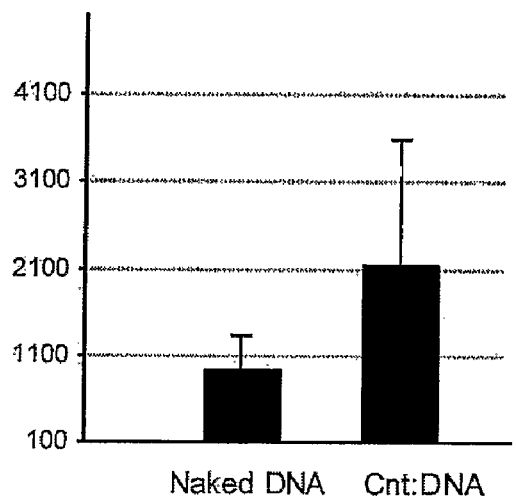
Figure 5C:
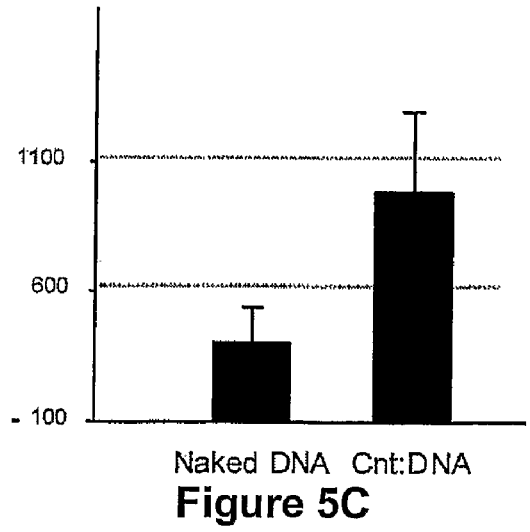

Briefly, all experimental animal studies were conducted with prior approval and under the regulations stated by the UK Home Office. 8-10 week old, male BALB/c mice were anesthetized by isoflorane inhalation. 1.5 ml of nanotube: DNA complexes containing 50 μg of DNA, and 50 μg DNA in 1.5 ml normal saline as a control were administered. Mice were injected via the tail vein by rapid hydrodynamic injection as previously described in Lecocq et al. (2003) J. Gene Med. 5:142-156. Mice were then euthanized 16 hours later and lung, liver, and spleen were harvested. Tissues were frozen at −80° C. overnight, thawed then homogenized in a lysis buffer containing 25 mM Tris-HCl pH 7.8, 2 mM DTT, 2 mM EGTA, 10% glycerol, and 1% Triton X-100 (all from Sigma). Luciferase activity was determined using the Tropix Luc-Screen Assay kit and a Berthold 9507 luminometer. Samples were corrected for total protein content using the Pierce BCA Assay kit. Experiments were performed using 3 animals per group and all assays in quadruplicate samples The results are presented in FIGS. 5A-5C, which show that interaction between the amino-functionalized SWNT and plasmid DNA does not impede in vivo gene expression levels following tail vein hydrodynamic administration. Luciferase gene expression levels in all three tissues exhibited a moderate (statistically insignificant for the liver tissue expression) upregulation at 24 hours post-administration, when DNA was complexed with ƒ-SWNT. Interestingly, from the expression data in the lung and spleen tissues, there is a 2-3 times enhancement in luciferase expression for the ƒ-SWNT:DNA, indicating an alteration in the biodistribution of DNA compared to naked plasmid DNA administration. More importantly though, particularly since this is the first in vivo gene delivery study undertaken using carbon nanotubes, the tubes do not at all seem to downregulate gene expression in any of the three tissues, while all animals exhibited no adverse reactions to the gene delivery systems despite the extremity of the hydrodynamic administration protocol. Further studies are needed though, in order to optimize and evaluate the efficiency and enhancement of gene expression that can be offered by carbon nanotubes as components of gene delivery vector systems. The data reported in the present study constitute the first example of carbon nanotubes utilized as components for engineering a novel nanotube-based gene delivery vector system. The functionalized nanotubes used, were shown to be able to interact and incorporate within cells in what seems to be an endosome-independent mechanism. Cytotoxicity assays showed that functionalized nanotubes are tolerated by cells up to concentrations of 10 mg/ml, much higher than those used for typical gene transfer applications (in the present gene delivery experiments the highest nanotube concentration used was 3 mg/ml). Moreover, ƒ-SWNT interacted with plasmid DNA to facilitate higher DNA uptake and gene expression in vitro compared to DNA alone. Levels were not as high as commercially available gene transfection agents, however they are shown to be capable of optimization. More interestingly, in vivo gene expression by tail vein hydrodynamic injection was not compromised and was well tolerated by all animals. Therefore, functionalized carbon nanotubes can be further explored as novel nanomaterials for construction of gene delivery vectors, exhibiting perfectly acceptable levels of cytotoxicity in vitro and no sign of adverse effects in vivo while maintaining beneficial levels of gene expression.

Example 4

The amino-functionalized SWNT (SWNT-NH$_3^+$ 1) complexed to HBsAg-coding plasmids (pRc/CMV-HBs(S), FIG. 7) were used for vaccination experiments in mice.

Briefly, control experiments were first performed on 4 groups of 6 Balb/c mice aged 6-8 weeks which were respectively immunized by intramuscular (IM) injection with:
PBS
pRc/CMV-HBs(S) (10 µg/mouse)
pRc/CMV-HBs(S) (100 µg/mouse)
Plasmid without the insert HBs (100 µg/mouse)

The immunogenes are suspended in 100 µl of PBS. Each mouse receives one bilateral injection (50 µl) on each muscle of the tibia of the back legs. The induced cellular response is then analyzed 10 days after the administration.

In experiments with pRc/CMV-HBs(S)/ƒ-SWNT complexes, an administration of the plasmid adsorbed on the ƒ-SWNT at different negative/positive charge ratios is performed for each route of immunization and each amount of plasmid. Three negative/positive charge ratios of pRc/CMV-HBs(S)/ƒ-SWNT complexes are used: 1:1, 1:2 and 1:6.

Thus, 9 groups of 6 Balb/c, mice of 6-8 weeks were respectively immunized with:
PBS
pRc/CMV-HBs(S)/ƒ-SWNT negative/positive charge 1:1 (10 µg/mouse of plasmid)
pRc/CMV-HBs(S)/ƒ-SWNT negative/positive charge 1:2 (10 µg/mouse of plasmid)
pRc/CMV-HBs(S)/ƒ-SWNT negative/positive charge 1:6 (10 µg/mouse of plasmid)
pRc/CMV-HBs(S)/ƒ-SWNT negative/positive charge 1:1 (100 µg/mouse of plasmid)
pRc/CMV-HBs(S)/ƒ-SWNT negative/positive charge 1:2 (100 µg/mouse of plasmid)
pRc/CMV-HBs(S)/ƒ-SWNT negative/positive charge 1:6 (100 µg/mouse of plasmid)
ƒ-SWNT alone (amount corresponding to the dose of the 1:6 ratio)
Plasmid without the insert HBs complexed to ƒ-SWNT (1 negative/positive charge ratio established on the basis of the control experiment)

Mice receive bilateral intramuscular (IM) injections once of 5 or 50 µg plasmid DNA suspended in 50 µl PBS into each anterior musculus tibialis. Control mice are injected IM with 2×50 µl PBS containing 100 µg plasmid without the HBs insert.

Alternatively, the same protocol can be repeated using the subcutaneous (SC) injection (200 µl PBS containing 10 or 100 µg of plasmid or the different complexes with ƒ-SWNT) at the base of the tail.

The induced cellular response is analyzed 10 days after the administration (3 mice) while the humoral response is studied after 10 weeks (3 mice). Serum samples are collected every 15 days after the administration of the immunogens along the period of 10 weeks to study the evolution of the antibody response. The animals are killed after 10 weeks to test the cellular response.

The anti-HBs humoral immune response is measured as described in Yoon et al., 1999, J Korean Med. Sci. 14:187-92. Briefly, anti-HbsIgG antibody production in the sera of IM and SC immunized mice are measured by ELISA method. ELISA plates are coated overnight at 4° C. with 1 µg/ml of HBV pre S2 antigen (a.a. 120-145, Sigma, H-7395, USA) dissolved in 0.05M carbonate-bicarbonate buffer (pH 9.6). Blocking was done by incubating the plates for 2 h at 37° C. with 200 µl of blocking solution (0.5% BSA dissolved in 0.05% Tween20-PBS). Mice sera were serially 2-fold diluted from 1:50 to 1:1600 in the antibody buffer (0.5% BSA solution in 0.05% Tween20-PBS) and 100 µl of the diluted sera are applied to the plates which are incubated for 1 h at 37° C. Horsedish peroxidase (HRP)-conjugated goat anti-mouse IgG antibody (Jackson Immuno-Research Laboratories Inc. West Grove, Pa.) diluted to 1:1000 in antibody buffer, is used as a secondary antibody and the plate was further incubated for 1 h at 37° C. After washing, the final reaction was visualized by adding 150 µl/well substrate solution (10% citric phosphate buffer pH 5, +0.04% $H_2O_2^+$ 90% of a solution containing 72 ml dimethylsulphoxide+18 ml glycerol+300 mg 3,3',5,5'-tetramethylenebenzidine) for 15 min at 37° C. The reaction was stopped with 0.25 M HCl, and absorbance was measured at 450 nm. Data are expressed as antibody titers corresponding to the reciprocal dilution giving an OD equal to 0.2.

Determination of splenic CTL frequencies is performed as described in Kwissa et al., 2003, J. Mol. Med. 81:91-101. Briefly, spleens were aseptically removed and pooled. Single-cell suspensions were prepared by gentle passage of the tissue through sterile mesh screens (100 µm). Erythrocytes were lysed with Tris-buffered ammonium chloride and the remaining cells were washed extensively in RPMI 1640 with 50 µM β-mercaptoethanol, 100 IU/ml gentamicin and 25 mM HEPES (complete medium, CM). Splenocytes were either used directly for FACS analysis and Elispot assay. Spleen cells (1×10$^7$/ml) are then incubated for 1 h in RPMI-1640 medium with 5 µg/ml HBsAg-derived, synthetic, $L^d$-binding $S_{28-39}$ IPQSLDSWWTSL peptide or $D^d$-binding $S_{201-209}$ WGPSLYSIL peptide. Thereafter 5 µg/ml brefeldin A (sigma 15870) was added, and the cultures were incubated for further 4 h. Cells were harvested and surface stained with phycoerythrin-conjugated anti-CD8 monoclonal antibody. Surface stained cells were fixed with 2% paraformaldehyde in phosphate buffered solution before intracellular staining for IFNγ. Fixed cells were resuspended in permeabilization buffer (Hank's balanced salt solution, 0.5% bovine serum albumin, 0.5% saponin, 0.05% sodium azide) and incubated with fluorescein isothiocyanate conjugated anti-IFNγ monoclonal antibody for 30 min at room temperature and washed three times in permeabilization buffer. Stained cells were resuspended in phosphate-buffered solution/0.3% w/v bovin serum albumine supplemented with 0.1% w/v sodium azide. The frequencies of CD8$^+$ IFNγ$^+$ CTL are determined by flow cytometry analyses.

Elispot-IFNγ are performed as follows. Nitrocellulose microplates (Millipore, Molsheim, France) were coated with rat anti-mouse IFNγ antibody (R4.6A2, PharMingen, Le Pont de Claix, France), and then washed and saturated with CM-10% FCS. Duplicate aliquots of effector cells (freshly isolated 1×10$^6$ splenocytes/well) were added to the wells containing CM-10% FCS with 30 U/ml human rIL2 (Boehringer Mannheim). Effector cells were incubated with 10 μg/ml HBsAg-derived, synthetic, $L^d$-binding $S_{28-39}$ IPQSLDSWWTSL peptide or $D^d$-binding $S_{201-209}$ WGPSLYSIL peptide. After 20 h at 37° C., biotinylated rat antimouse IFNγ mAb (XMG1.2, PharMingen) was added for overnight incubation. After washing, alkaline phosphatase labeled ExtrAvidin (Sigma) was added and wells were incubated for 1 h at room temperature. Finally, alkaline phosphatase conjugate substrate (Bio-Rad Laboratories, Hercules, Calif.) was added for 30 min. Spot-forming cells were counted using a computer-assisted video image analyzer (Zeiss-Kontron, Jena, Germany).

Example 5

In this example, the capacity of functionalized carbon nanotube (f-CNT) complexed to DNA to transfect eukaryotic cells was studied.

Materials and Methods

General. Ammonium functionalized single-walled carbon nanotubes (SWNT-$NH_3^+$ 1), amino functionalized multi-walled carbon nanotubes (MWNT-$NH_3^+$ 2), and lysine functionalized single-walled carbon nanotubes (SWNT-Lys-$NH_3^+$ 3), as depicted in FIG. 1, were prepared as described in Example 1.

Ammonium-functionalized, single- (1) and multi-walled carbon nanotubes (2) were solubilized in deionized water at a concentration of 6 mg/ml and 6.6 mg/ml, respectively. Lysine-functionalized single-walled carbon nanotubes (3) were dissolved in deionized water at a concentration of 3.3 mg/ml. All solutions were sonicated for 1 min at room temperature in a bath sonicator (80W, EMscope Laboratories, UK), then stored at 4° C. until needed. Prior to use, nanotube solutions were briefly sonicated once again. The plasmid used for these studies was pCMV-Bgal (BD-Clontech, U.K.), a 7.2 kb, eukaryotic expression vector. A gigaprep of highly-purified supercoiled DNA was prepared by Bayou Biolabs (LA, USA). A stock solution was prepared in deionised water at a concentration of 1 mg/ml. Aliquots were stored frozen at –80° C. until use.

ƒ-CNT:DNA complexes. To prepare the functionalized carbon nanotube (ƒ-CNT):DNA complexes, the appropriate volume of each type of nanotube was diluted to a total volume of 200 μl in deionized water, then split into four 50 μl aliquots for each concentration of ƒ-CNT. Depending on the type of nanotube and charge ratio needed, ƒ-CNT concentrations ranged from 16.5 μg/ml to 300 μg/ml. An equal volume of a 5 μg/ml DNA solution was then added to three of the ƒ-CNT aliquots then mixed by rapidly pipetting 10 times, yielding a final DNA concentration of 250 ng/ml. 50 μl of deionized water was added to the fourth ƒ-CNT aliquot of each group as a nanotube-only control. Complexes were allowed to form for 30 min at room temperature prior to use. This process was repeated for each charge ratio tested, yielding three samples per condition plus a nanotube-only sample at the corresponding concentration.

Scanning electron microscopy. SEM was used to image the SWNT-$NH_3^+$ 1 and MWNT-$NH_3^+$ 2 complexed with the plasmid DNA. Imaging was carried out by placing a 30 μl drop of the 6:1 (CNT:DNA) charge ratio complex samples or an equivalent concentration of nanotubes alone onto the SEM stub and allowed to dry at room temperature prior to gold coating. This was performed in an Emitech K550 Sputter Coater for 2 min at 20 mA. Imaging was carried out under a FEI/Philips XL 30 Scanning Electron Microscope (Eindhoven, The Netherlands) at an accelerating voltage of between 20-25 KV (see also on each image). Images were captured and saved digitally.

Surface plasmon resonance. The BIAcore 3000 system, sensor chip CM5, surfactant P20, amine coupling kit containing N-hydroxysuccinimide (NHS) and N-ethyl-N'-dimethylaminopropyl carbodiimide (EDC) were from BIAcore (Uppsala, Sweden). All biosensor assays were performed with HBS as running buffer (20 mM HEPES, 20 mM sodium acetate, 140 mM potassium acetate, 3 mM magnesium acetate, 0.02% surfactant P20, pH 7.3). Immobilization of nanotubes was performed by injecting 35 μl of nanotubes (100 μg/ml in acetate buffer, pH 4.0) onto the surface of a sensor chip CM5 activated with EDC/NHS. This was followed by 20 μl of ethanolamine hydrochloride, pH 8.5, to saturate the free activated sites of the matrix. A 100 mM $H_3PO_4$ solution was used to remove nanotubes non-covalently immobilized on the chip. All the binding experiments were carried out at 25° C. with a constant flow rate of 30 μl/mn. pCMV-BGal was dissolved in the running buffer. Different concentrations of plasmid (6.3 to 100 μg/ml) were injected for 90 sec, followed by a dissociation phase of 2 min. In all experiments, the sensor chips were regenerated with 15 μl of 3 M $MgCl_2$. The kinetic parameters were calculated using the BIAeval 3.1 software. Analysis was performed using the simple Langmuir binding model. The specific binding profiles were obtained after subtracting the response signal from the channel control. The fitting to each model was judged by the chi square value and randomness of residue distribution compared to the theoretical model.

Pico Green assay for ƒ-CNT:DNA complexes. The degree of DNA accessibility following complexation with ƒ-CNT was assessed by the double-stranded-DNA-binding reagent PicoGreen (Molecular Probes, Oreg., U.S.A.). Briefly, the carbon nanotube:DNA complexes were diluted 10× with deionized water to yield a final DNA concentration of 250 ng/ml, then 100 μl of sample was added to triplicate wells of a CoStar 96-well special optics black plate (Corning, N.Y., USA). Because the plasmid used for this study, pCMV-Bgal primarily is in a supercoiled state, a standard curve ranging from 1000 ng/ml to 31.25 ng/ml was generated using this plasmid rather than the control included with the assay kit. 100 μl of PicoGreen reagent in 2×TE buffer (20 mM Tris/HCl/2 mM EDTA, pH 7.5) was added in each well and the plate was incubated in the dark for three minutes, then measured at excitation and emission wavelengths of 485 and 530 nm respectively, using a Wallac Victor (Wallac, UK) multi-well plate reader. Because the carbon nanotubes alone autofluoresce at the measured wavelength, a second standard curve of carbon nanotubes alone was generated to quantify the background fluorescence. This was then subtracted from each sample. Percent free DNA was determined by dividing the background-corrected PicoGreen counts of each complex by the background-corrected measurement of 250 ng/ml of pBgal alone, representing 100% free DNA. Data are expressed as the mean of three samples, plus or minus standard deviation.

Electrophoretic Motility Shift Assay. 0.2 μg of DNA (pBgal) complexed to the three types of carbon nanotubes at different charge ratios, or 0.2 μg free DNA as a control was added to a 1% agarose gel in TAE buffer containing ethidium bromide. The gel was run for 2 h at 90V, then photographed under UV light using a UVP Gel Documentation System (Upland, Calif., USA). Each sample was run in duplicate.

Gene Transfer Study. A549 cells (ATCC, Middlesex, UK) were grown in DMEM containing 10% FBS and 1% penicillin/streptomycin (all from Invitrogen/Gibco, Paisley, UK) until just confluent in 96 well plates. Complexes were formed by diluting 0.75 µg of pCMV-Bgal in serum-free DMEM, then by diluting the appropriate amount of SWNT-$NH_3^+$ 1, MWNT-$NH_3^+$ 2, or SWNT-Lys-$NH_3^+$ 3 in 75 µl of serum-free DMEM to yield the indicated charge ratios with 0.75 µg DNA. The DNA solution was mixed with $f$-CNT by rapid pipetting and allowed to stabilize for 30 min. The complete media was removed from the A549 cells and replaced with 150 µl of the various $f$-CNT:DNA complexes. Cells treated with media alone, or media containing 0.75 µg of DNA were used as control. Cells were incubated with the complexes for 90 min at 37° C., and then the transfection media was removed and replaced with complete media. Cells were left for 48 h, washed one time in PBS, lysed, and analysed for β-galactosidase expression using the Tropix Galactolight Plus Kit (Applied Biosystems, CA, U.S.A) and a Lumat LB 9507 luminometer (Berthold Technologies, Bad Wildbad, Germany). Data are expressed as the mean of triplicate samples after subtraction of the DNA only group, plus/minus the standard deviation of the mean.

Results

In order to visualize the complexes formed following the interaction of $f$-CNT with plasmid DNA, both SWNT-$NH_3^+$ 1 and MWNT-$NH_3^+$ 2 were analyzed in the presence (FIG. 8A-8F) of the β-gal expressing plasmid by scanning electron microscopy (SEM).

Earlier observations (Example 2) demonstrated that SWNT-$NH_3^+$ 1 at a concentration of 180 µg/ml in aqueous solution complexed to plasmid DNA at a concentration of 5 µg/ml (yielding a 6:1 charge ratio) produced peak levels of gene expression in vitro. In the present study the same conditions were used to examine the physical and morphological characteristics of the resulting complexes by SEM. MWNT-$NH_3^+$ 2, due to differences in the loading of the available functional amino group (0.90 mmol/g of $NH_2$), were solubilized at a concentration of 99 µg/ml to yield an equivalent charge ratio when complexed to the same DNA concentration. When carbon nanotube:DNA complexes were formed at a 6:1 charge ratio, very clear images of aggregated structures were observed throughout the SEM sample grids (FIG. 8A-8F).

MWNT-$NH_3^+$:DNA complexes formed aggregates larger than 4 µm and possessed a planar lattice structure. DNA condensates form a concrete-like planar structure with nanotubes buried within (FIGS. 8A-8C). The DNA appears much more tightly packed, without well defined edges separating the concrete-like block. SEM images of the SWNT-$NH_3^+$:DNA complexes presented different structural features, as evidenced by the formation of almost discrete aggregate particles of 1 to 4 µm in diameter around the $f$-SWNT (FIGS. 8D-8F). In this case the single-walled carbon nanotubes seemed to form a parallel lattice, with sphere-like DNA bundles interlocking the individual tubes, while their ends can be seen extending from the edges of the complex. The SWNT-$NH_3^+$:DNA complexes were characterized by well defined, spherical structures rather than the concrete-like lattice observed in the case of MWNT-$NH_3^+$:DNA, which the Inventors believe is due to different structures attained by the condensed plasmid DNA around the cationic nanotubes. This difference may be ascribed to both the greater cationic charge density on the surface of the MWNT-$NH_3^+$ and the increased surface area which allow the DNA to associate more closely with the nanotubes themselves.

In an attempt to quantify the affinity between the functionalized carbon nanotubes and plasmid DNA, their interactions were measured by Surface Plasmon Resonance (SPR). For this study, a second type of $f$-CNT was also introduced, which corresponds to SWNT-Lys-$NH_3^+$ 3 (FIG. 1). The nanotubes of FIG. 1 were immobilized onto the sensor chip by forming a stable amide bond between the $NH_2$ on the tubes and the carboxylic functions on the chip's gold surface, activated in turn with carbodiimide and N-hydroxysuccinimide. This first step was followed by an acidic washing treatment to remove all reagents and excess of carbon nanotubes. The covalent immobilization of the nanotubes was demonstrated by a clear increase in the sensorgram response.

In the case of both SWNT-$NH_3^+$ 1 and SWNT-Lys-$NH_3^+$ 3, the amount of fixed tubes was significantly reduced after extensive washings with 100 mM phosphoric acid. This could be due to a non specific binding of a certain amount of nanotubes onto the sensor chip. The acid treatment had no effect on the MWNT-$NH_3^+$ 2, since no significant decrease of the resonance units was detected. To better characterize the functionalization of the sensor chip with the nanotubes, SEM analysis of the sensor chip was carried out. Using this technique, the nanotubes could visualized covalently linked to the chip's surface. FIG. 9 clearly shows the SEM image of MWNT-$NH_3^+$ 2 on top of the carboxymethylated dextran layer that coats the sensor chip surface. The tubes range in diameter between 20 and 70 nm and they are present as single entities.

After immobilization of the different tubes onto the sensor chip, their interaction with the plasmid DNA, pCMV-Bgal, was examined. The plasmid was used at different concentrations in the injected buffer (6.3-100 µg/ml). For each concentration, the association and dissociation curves were fitted separately using a simple Langmuir model. The sensorgram data for the association of the plasmid with the SWNT-Lys-$NH_3^+$ 3 and the MWNT-$NH_3^+$ 2 are summarized in FIG. 10. Analysis of the fitting parameters enabled us to calculate an apparent equilibrium association constant of $4.45 \times 10^8$ and $2.36 \times 10^7$ $M^{-1}$ for the SWNT-Lys-$NH_3^+$ 3 and the MWNT-$NH_3^+$ 2, respectively.

SPR (response expressed as resonance units) allows detection of complexes in the fluid phase up to 100 nm above the gold surface. Under the hypothesis that the overall interaction between the immobilized carbon nanotubes and the plasmid DNA can be generally represented by those interactions detected within the signal-sensitive area above the gold surface (100 nm thickness), it is possible to calculate the positive:negative charge ratio between the two participating components. Simple conversion of RU values (1 RU=1 picogram/$mm^2$) indicates charge ratios of 62.5:1 and 11.5:1 (+/−) for the SWNT-Lys-$NH_3^+$:DNA and the MWNT-$NH_3^+$:DNA complexes, respectively. MWNT-$NH_3^+$ are able to condense a larger amount of DNA in comparison to the SWNT-Lys-$NH_3^+$. The difference is certainly due to the relative dimensions of the two types of nanotubes, because the charge density is almost the same in both systems. The MWNT offer a higher available surface for interaction with the DNA. From the SPR study, it can be concluded that the $f$-CNT have a strong affinity for the plasmid DNA, forming a supramolecular complex which is stabilized by strong ionic interactions. The electrostatic interaction is fully reversible as confirmed by the complete dissociation of plasmid during the regeneration process of the sensor chip with magnesium chloride.

An alternative technique was used to study the $f$-CNT:DNA complexes. The PicoGreen dye exclusion assay can be used to evaluate the degree of DNA compaction by the nanotubes in solution. PicoGreen fluorescence increases approximately 1000-fold upon intercalation between dsDNA base pairs. When DNA is condensed, the dye is prevented from interacting with it; thus, a decrease in fluorescence is observed when condensed DNA is compared to an equal concentration of free DNA.

The interaction of all three types of $f$-CNT described in this study was assessed with DNA over a range of charge ratios as indicated in FIGS. 11A-11C. The concentration of plasmid DNA during complex formation remained constant at 2.5 µg/ml, while the concentration of the nanotubes ranged from 8.25 µg/ml to 150 µg/ml, depending upon the type of tube and the charge ratio examined. In all three cases, $f$-CNT are clearly able to compact DNA. SWNT-NH$_3^+$ 1 (FIG. 11A) appear the least efficient in compacting DNA. At a charge ratio of 1:1, only 43% of DNA is condensed, gradually increasing to 58% at 6:1. Little to no further condensation appears to occur at higher charge ratios. More than 96% of DNA is condensed by MWNT-NH$_3$+2 (FIG. 11C) at a charge ratio of 1:1 and 99% of DNA is condensed at a charge ratio of 6:1 and above. In the case of SWNT-Lys-NH$_3^+$ 3 (FIG. 11B) which have a similar surface charge load as MWNT-NH$_3^+$, approximately 74% of DNA appears condensed at a 1:1 charge ratio, gradually increasing to 85% at 6:1, reaching maximum condensation at 10:1, where more than 92% of DNA is condensed.

Figure 8:
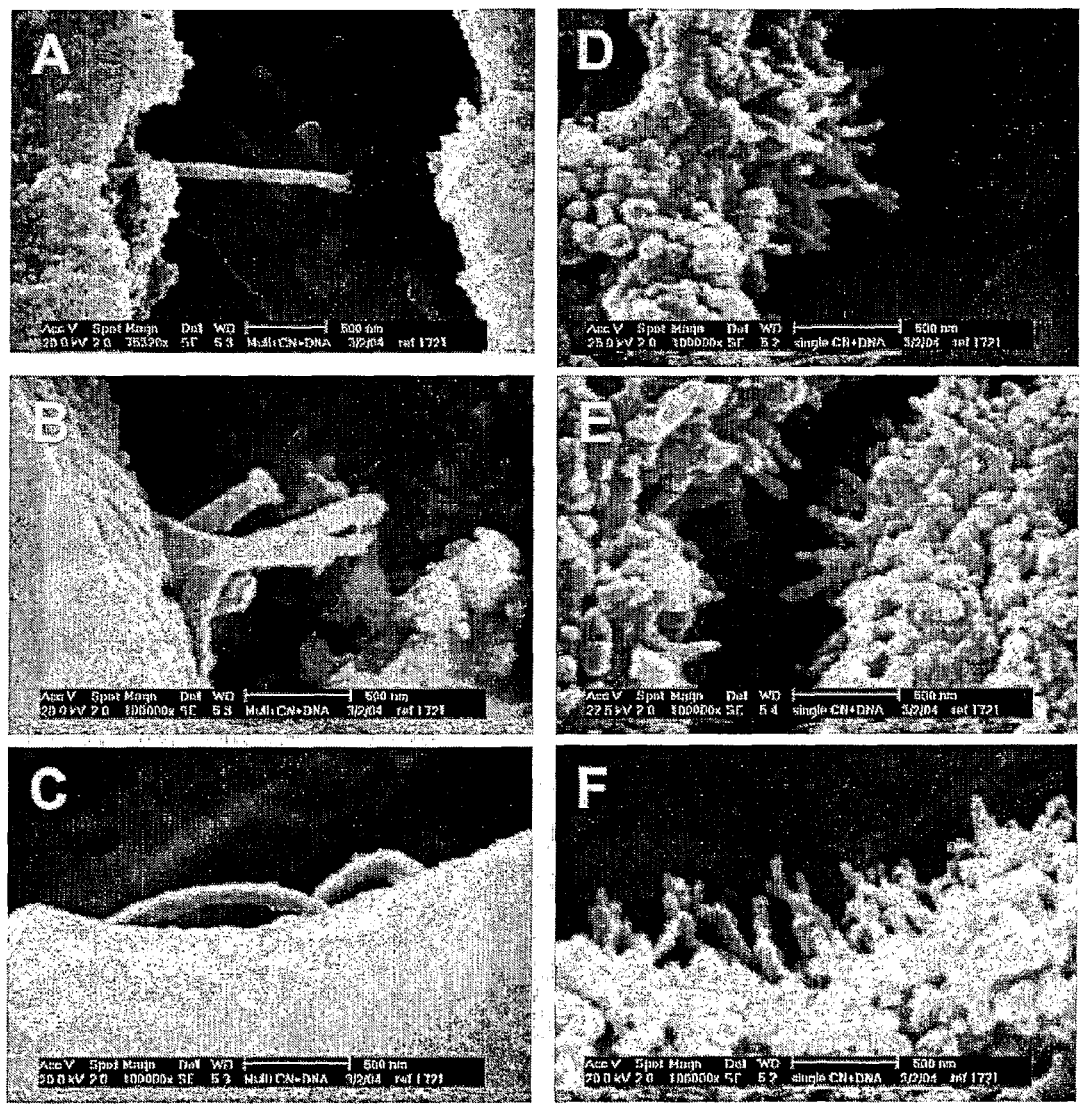

The PicoGreen data confirm the observation of the apparently less dense packing of the DNA following interaction with the SWNT-NH$_3^+$ compared to the MWNT-NH$_3^+$ as seen in the SEM images (FIG. 8). This is thought to be due to the lower charge loading efficiency and the relatively restricted access to the positive charges available on the SWNT-NH$_3^+$ when compared to the other types of $f$-CNT. Likewise, the MWNT-NH$_3^+$ appear to condense DNA most efficiently.

Next, the migration of the $f$-CNT:DNA complexes was studied by agarose gel electrophoresis and the degree of DNA condensation by EtBr (ethidium bromide) exclusion (FIGS. 12A-12C). The plasmid pCMV-βgal used in these studies, was highly purified such that approximately 85% was supercoiled with the remaining 15% in an open circular form (lane 1, FIG. 12A). The condensation of DNA by $f$-CNT excludes EtBr intercalation, quenching the fluorescence signal. Therefore, it was not possible to observe condensed DNA participating in the $f$-CNT:DNA complexes. In general, the fluorescent bands observed in FIGS. 12A-12C originate from free (uncomplexed) DNA which allows for adequate EtBr intercalation. FIGS. 12A-12C also reveals an overall decrease in the fluorescence intensity of the free DNA bands with increasing $f$-CNT:DNA charge ratio, due to reduced availability of DNA bases for EtBr intercalation caused by the higher degree of DNA condensation. Typically, this assay is used to study the migration of different types of DNA conformations as indicated by a shift in their migration rate. In the present case, this was possible only in the case of SWNT-NH$_3$ (FIG. 12A) which does not seem to be able to fully condense DNA. In lanes 2, 3 and 4 different conformations of free DNA were evident, which can include nicked DNA.

It was also found that the data in FIGS. 12A-12C are in striking agreement with the previous experiments. In the case of SWNT-NH$_3^+$:DNA, a strong fluorescent signal is observed in lane 2, corresponding to the 1:1 charge ratio (FIG. 12A), indicating the presence of a large amount of free DNA. There is a strong decrease in the fluorescence intensity and an increase in the upward shift of the free DNA bands as the charge ratio is increased to 6:1, but little difference is observed when the +/− charge ratio is further increased to 10:1. This is expected as the PicoGreen data indicated that the amount of complexed DNA reaches a plateau at this range (see also FIG. 11A). Complexation between SWNT-Lys-NH$_3^+$ 3 and DNA (FIG. 12B) is stronger as observed by the overall weaker fluorescence intensity of the free DNA bands when compared to those of the SWNT-NH$_3^+$:DNA, and the gradual disappearance of fluorescence with increasing charge ratios, indicating even further reduction in the amount of free DNA available for intercalation. In the case of MWNT-NH$_3^+$ 2, we can only see a faint fluorescent signal at the 1:1 charge ratio due to the very small amounts of free DNA present (lane 2, FIG. 12C; see also FIG. 11C). In the same lane we believe the faint smear detected is due to DNA that interacts with the MWNT-NH$_3^+$ 2 but is not fully condensed, allowing for some EtBr intercalation, also indicating the wide mass distribution of these complexes. For higher MWNT-NH$_3^+$:DNA ratios the fluorescence band disappears since the entire amount of DNA is fully condensed.

Although there appears to be an upward shift in the location of the free DNA band when $f$-CNT are present in the gel, this is most likely caused by alteration of the running buffer due to the high ionic strength of the nanotubes themselves. While it is possible that this shift may be due to nicking of the supercoiled DNA, either due to interaction with nanotubes or sustained during the mixing process, causing the DNA to relax to a more open form, control studies in which high concentrations of SWNT-NH$_3^+$ 1 alone (12 mg/ml) were run in bluegreen loading buffer demonstrated a clear retardation of the dye's movement indicating that the ionic strength of the running buffer can be responsible for changes in the migration of molecules in the gel.

Finally, the gene transfer efficiency of the various $f$-CNT: DNA complexes formed was studied. The data demonstrate that all three types of complexes are able to transfect A549 cells with greater efficiency than naked DNA, which was normalized to a zero value in all three figures (FIGS. 13A-13C). SWNT-NH$_3^+$ 1 appear to be most efficient at gene transfer when complexed to DNA at an 8:1 charge ratio, while SWNT-Lys-NH$_3^+$ 3 appear most efficient at a 1:1 charge ratio. Interestingly, the Pico Green data indicate that at these charge ratios, approximately 30% of DNA is free to interact with the dye in the case of SWNT-NH$_3^+$ 1, and a similar 25% of DNA is free in the case of SWNT-Lys-NH$_3^+$ 3. This data indicates that an optimum degree of DNA condensation by $f$-CNT may lead to higher levels of gene expression. Not surprisingly, in the case of MWNT-NH$_3^+$ 2 since even at very low charge ratios DNA is fully condensed, there does not appear to be much difference in the transfection efficiency of these nanotubes across all charge ratios and DNA dose studied. It is important to note that while the transfection efficiency of the SWNT-Lys-NH$_3^+$ 3, which at high charge ratios condensed 95% of DNA, appears to decrease with increasing charge ratio, the same effect is not found with the MWNT-NH$_3^+$ 2 group, which as noted, maintains similar levels of transfection efficiency across all charge ratios. This may be an indication that the structure of the multi-walled nanotubes, which are both longer and wider than the single walled tubes, may also be playing a critical role.

Example 6

Carbon nanotubes functionalized with DTPA at a concentration between 10 and 100 µg/ml in water are mixed with a protein at a concentration between 0.1 and 1 µM in PBS buffer for 2 hours. Proteins comprise for example streptavidin, protein A, bovine serum albumin, cytochrome c. In particular, proteins with isoelectric point major than 7 are ideal to fully exploit the attraction electrostatic interactions. The complexes are characterized by TEM and AFM and subsequently delivered to cells.

The invention claimed is:

1. A method for the manufacture of a complex between a carbon nanotube comprising positive or negative charges, said charges being carried by at least one charge-carrying group, said charge-carrying group being covalently bound to the surface of said carbon nanotube, and at least one charged molecule, provided that the charged molecule is different from Cl$^-$ and TFA$^-$, wherein the bond between the carbon nanotube and the charged molecule is essentially electrostatic, and said charged molecule comprising at least one negative charge if said carbon nanotube comprises positive charges or at least one positive charge if said carbon nanotube comprises negative charges.

2. A method for the manufacture of a complex between a carbon nanotube comprising positive or negative charges, said charges being carried by at least one charge-carrying group, said charge-carrying group being covalently bound to the surface of said carbon nanotube, and at least one charged molecule having a molecular weight greater than 115, wherein the bond between the carbon nanotube and the charged molecule is essentially electrostatic, and said charged molecule comprising at least one negative charge if said carbon nanotube comprises positive charges or at least one positive charge if said carbon nanotube comprises negative charges.

3. A complex comprising:
a carbon nanotube comprising positive or negative charges, said charges being carried by at least one charge-carrying group, said charge-carrying group being covalently bound to the surface of said carbon nanotube, and
at least one charged molecule, said charged molecule comprising at least one negative charge if said carbon nanotube comprises positive charges or at least one positive charge if said carbon nanotube comprises negative charges, provided that the charged molecule is different from Cl$^-$ and TFA$^-$,
the bond between the carbon nanotube and the charged molecule being essentially electrostatic.

4. A complex comprising:
a carbon nanotube comprising positive or negative charges, said charges being carried by at least one charge-carrying group, said charge-carrying group being covalently bound to the surface of said carbon nanotube, and
at least one charged molecule having a molecular weight greater than 115, said charged molecule comprising at least one negative charge if said carbon nanotube comprises positive charges or at least one positive charge if said carbon nanotube comprises negative charges,
the bond between the carbon nanotube and the charged molecule being essentially electrostatic.

5. The complex according to claim 3, wherein said complex is soluble in aqueous solvents and non-toxic.

6. The complex according to claim 3, wherein the binding energy between a charged molecule and the carbon nanotube is lower than 90 kJ/mol.

7. The complex according to claim 3, wherein the carbon nanotube comprises either positive charges or negative charges and the charged molecule comprises respectively either at least one negative charge or at least one positive charge.

8. The complex according to claim 3, wherein the carbon nanotube comprises either positive charges or negative charges and the charged molecule comprises respectively either at least one negative charge or at least one positive charge and said carbon nanotube comprises from 0.001 to 100 charges, per charge of the charged molecule.

9. The complex according to claim 3, wherein the carbon nanotube is substantially intact and soluble in organic or aqueous solvents in the presence or absence of the charged molecule, and that the charge-carrying groups are homogeneously distributed on the surface of said carbon nanotube.

10. The complex according to claim 3, wherein the carbon nanotube is a single-walled (SWNT) or a multi-walled carbon nanotube (MWNT).

11. The complex according to claim 3, wherein the carbon nanotube corresponds to the following general formula:

wherein:
$C_n$ are surface carbons of a substantially cylindrical carbon nanotube of substantially constant diameter, said diameter being from 0.5 to 50 nm, for SWNT and from 20 to 50 nm for MWNT,
X represents one or several functional groups, identical or different, provided that at least one of the X groups comprises at least one charge-carrying group,
n is an integer from $3 \times 10^3$ to $3 \times 10^6$,
m is an integer from 0.001 n to 0.1 n,
there are from $2 \times 10^{-11}$ moles to $2 \times 10^{-9}$ moles of X functional groups per cm$^2$ of carbon nanotube surface.

12. The complex according to claim 11, wherein X represents two different functional groups, $X^1$ and $X^2$, and the carbon nanotube corresponds to the following formula:

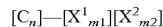

wherein, independently from each other, $m_1$ and $m_2$ represent integers from 0.001 n to 0.1 n, provided that at least one of $X^1$ or $X^2$ comprises at least one charge-carrying group.

13. The complex according to claim 11, wherein X represents one or more substituted pyrrolidine rings, identical or different, provided that at least one of said substituted pyrrolidine rings is substituted by at least one charge-carrying group, of the following general formula (I):

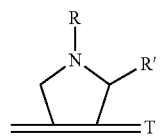

wherein T represents a carbon nanotube, and independently from each other R and R' represent —H or a group of formula -M-Y—(Z)$_a$—(P)$_b$, wherein a represents 0 or 1 and b represents an integer from 0 to 8, P representing identical or different groups when b is greater than 1, provided R and R' cannot simultaneously represent H, and:
M is a spacer group from 1 to 100 atoms, optionally comprising a charge-carrying group, said group being selected from —(CH$_2$)$_r$— or —(CH$_2$—CH$_2$—O)$_r$—CH$_2$—CH$_2$—, wherein r is an integer from 1 to 20,
Y is a reactive group when a=b=0, optionally comprising a charge-carrying group, said group being selected from —OH, —$_3^-$, —COO$^-$, —SH, —CHO, a ketone: —COCH$_3$, an azide or a halide,
or derived from a reactive group, when a or b is different from 0, optionally charged, said group being selected from —O—, —NH—, —COO—, —S—, —CH=, —CH$_2$—, or —CC$_k$H$_{2k+1}$=, wherein k is an integer from 1 to 10;

Z is a linker group, optionally comprising a charge-carrying group, liable to be linked to at least one P group, and if need be to release said P group, said group being selected from the following formulae when a=1 and b=0:

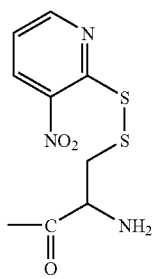

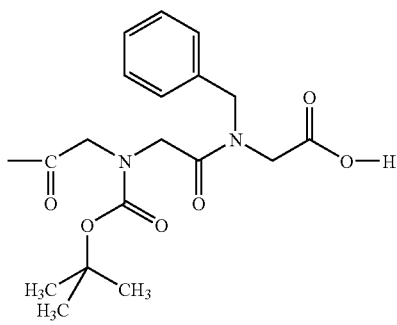

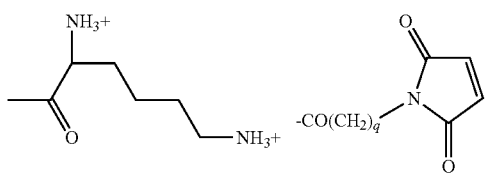

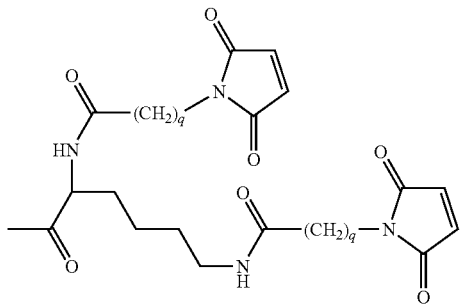

wherein q is an integer from 1 to 10;
or of one of the corresponding following formulae when a=1 and b=1 or 2:

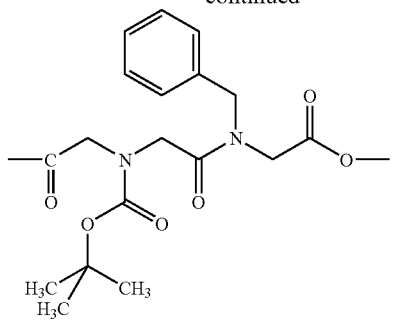

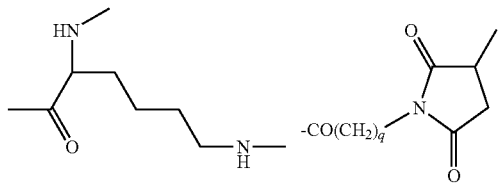

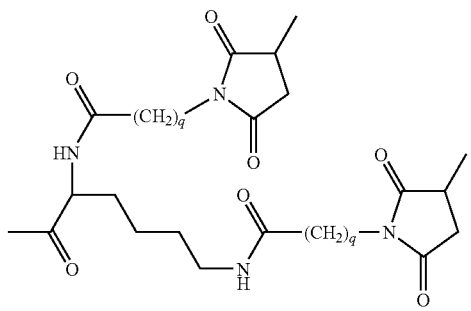

wherein q is an integer from 1 to 10;

P is an effective group, optionally comprising a charge-carrying group, allowing spectroscopic detection of said functionalized carbon nanotube, selected from the group consisting of: a fluorophore: FITC, a chelating agent: DTPA, and an active molecule, liable to induce a biological effect, said active molecule being selected from the group consisting of: an amino acid, a peptide, a pseudopeptide, a polypeptide, a protein, an enzyme or an antibody, a nucleic acid, a carbohydrate, and a drug;

if appropriate at least one of Y, Z, or P groups, can be substituted by a capping group selected from the list consisting of: $CH_3CO$— acetyl, methyl, ethyl, or benzylcarbonyl, or a protecting group selected from the list consisting of: methyl, ethyl, benzyl, tert-butyl, trityl, 3-nitro-2-pyridylsulfenyl, tert-butyloxycarbonyl, fluorenylmethyloxycarbonyl, benzyloxycarbonyl, benzoyl, trimethylsilylethyloxycarbonyl, phtalimide, dimethylacetal, diethylacetal, and 1,3-dioxolane.

14. The complex according to claim 13, wherein X represents two different substituted pyrrolidine rings, provided that at least one of said pyrrolidine rings is substituted by at least one charge-carrying group, of the following general formula (I'):

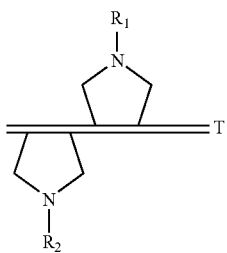

wherein T represents a carbon nanotube, $R_1$ and $R_2$ are different and represent, independently from each other, —H or a group of formula $-M-Y-(Z)_a-(P)_a-(P)_b$, at least one of $R_1$ and $R_2$ comprising a charge carrying group.

15. The complex according to claim 11, corresponding to the following general formula (II):

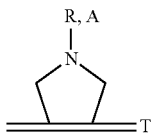

wherein T represents a carbon nanotube, A represents a charged molecule, and R represents a group of formula -M-W, and:

M is a spacer group from 1 to (about) 100 atoms, said group being selected from the list comprising —$(CH_2)_r$— or —$(CH_2-CH_2-O)_r-CH_2-CH_2$—, wherein r is an integer from 1 to 20;

W is a charge-carrying group from 1 to 400 atoms.

16. The complex according to claim 14, corresponding to the following general formula (II'):

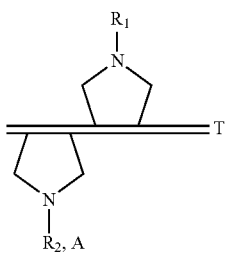

wherein T represents a carbon nanotube, A represents a charged molecule, and $R_1$ represents a group of formula $-M-Y-(Z)_a-(P)_b$ and, $R_2$ represents a group of formula -M-W, W being a charge-carrying group from 1 to 400 atoms.

17. The complex according to claim 3, wherein the charged molecule is selected from nucleic acids, selected from the group consisting of: RNA and DNA, having 2 to $10^6$ nucleotides, peptides, polypeptides or proteins, having 2 to 5000 amino acids, or carbohydrates, selected from the group consisting of: glucosamine and chitosane, radionucleides, and cytotoxic molecules.

18. A complex according to claim 3, corresponding to the following formula:

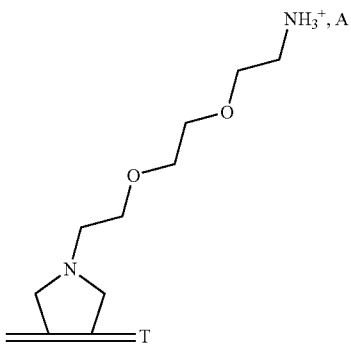

wherein T represents a carbon nanotube, and A represents a charged molecule, comprising at least one negative charge: DNA.

19. The complex according to claim 3, corresponding to the following formula:

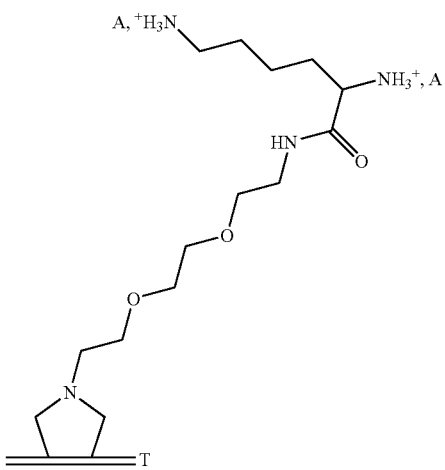

wherein T represents a carbon nanotube, and A represents a charged molecule, comprising at least one negative charge: DNA.

20. The complex according to claim 3, corresponding to the following formula:

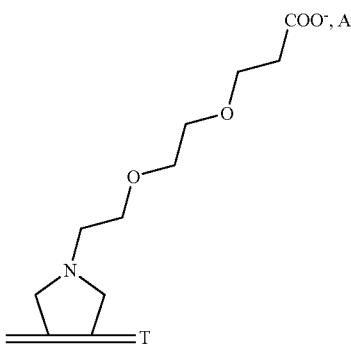

wherein T represents a carbon nanotube, and A represents a charged molecule comprising at least one positive charge.

21. The complex according to claim 3, corresponding to the following formula:

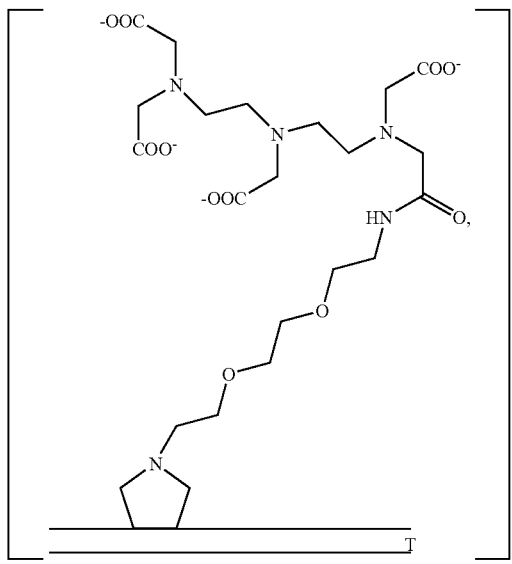

wherein T represents a carbon nanotube, and A represents a charged molecule comprising at least one positive charge.

22. A method of treatment of a patient in need thereof with the complex according to claim 3, for the delivery of the charged molecules into cells.

23. A pharmaceutical composition comprising as active substance a complex defined in claim 3, in association with an acceptable pharmaceutical carrier.

24. The complex according to claim 4, wherein said complex is soluble in aqueous solvents and non-toxic.

25. The complex according to claim 4, wherein the binding energy between a charged molecule and the carbon nanotube is lower than 90 kJ/mol.

26. The complex according to claim 4, wherein the carbon nanotube comprises either positive charges or negative charges and the charged molecule comprises respectively either at least one negative charge or at least one positive charge.

27. The complex according to claim 4, wherein the carbon nanotube comprises either positive charges or negative charges and the charged molecule comprises respectively either at least one negative charge or at least one positive charge and said carbon nanotube comprises from 0.001 to 100 charges, per charge of the charged molecule.

28. The complex according to claim 4, wherein the carbon nanotube is substantially intact and soluble in organic or aqueous solvents in the presence or absence of the charged molecule, and that the charge-carrying groups are homogeneously distributed on the surface of said carbon nanotube.

29. The complex according to claim 4, wherein the carbon nanotube is a single-walled (SWNT) or a multi-walled carbon nanotube (MWNT).

30. The complex according to claim 4, wherein the carbon nanotube corresponds to the following general formula:

$$[C_n]-X_m$$

wherein:

$C_n$ are surface carbons of a substantially cylindrical carbon nanotube of substantially constant diameter, said diameter being from 0.5 to 50 nm, for SWNT and from 20 to 50 nm for MWNT, X represents one or several functional groups, identical or different, provided that at least one of the X groups comprises at least one charge-carrying group, n is an integer from $3 \times 10^3$ to $3 \times 10^6$, m is an integer from 0.001 n to 0.1 n, there are from $2 \times 10^{-11}$ moles to $2 \times 10^{-9}$ moles of X functional groups per $cm^2$ of carbon nanotube surface.

31. The complex according to claim 30, wherein X represents two different functional groups, $X^1$ and $X^2$, and the carbon nanotube corresponds to the following formula:

$$[C_n]-[X^1{}_{m1}][X^2{}_{m2}]$$

wherein, independently from each other, $m_1$ and $m_2$ represent integers from 0.001 n to 0.1 n, provided that at least one of $X^1$ or $X^2$ comprises at least one charge-carrying group.

32. The complex according to claim 30, wherein X represents one or more substituted pyrrolidine rings, identical or different, provided that at least one of said substituted pyrrolidine rings is substituted by at least one charge-carrying group, of the following general formula (I):

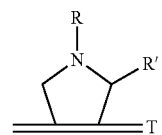

I wherein T represents a carbon nanotube, and independently from each other R and R' represent —H or a group of formula -M-Y—$(Z)_a$—$(P)_b$, wherein a represents 0 or 1 and b represents an integer from 0 to 8, P representing identical or different groups when b is greater than 1, provided R and R' cannot simultaneously represent H, and:

M is a spacer group from 1 to 100 atoms, optionally comprising a charge-carrying group, said group being selected from —$(CH_1)_r$— or —$(CH_2$—$CH_2$—$O)_r$—$CH_2$—$CH_2$—, wherein r is an integer from 1 to 20, Y is a reactive group when a=b=0, optionally comprising a charge-carrying group, said group being selected from —OH, —$NH_3^+$, —$COO^-$, —SH, —CHO, a ketone: —$COCH_3$, an azide or a halide, or derived from a reactive group, when a or b is different from 0, optionally charged, said group being selected from —O—, —NH—, —COO—, —S—, —CH=, —$CH_2$—or —$CC_kH_{2k+1}$=, wherein k is an integer from 1 to 10;

Z is a linker group, optionally comprising a charge-carrying group, liable to be linked to at least one P group, and if need be to release said P group, said group being selected from the following formulae when a=1 and b=0:

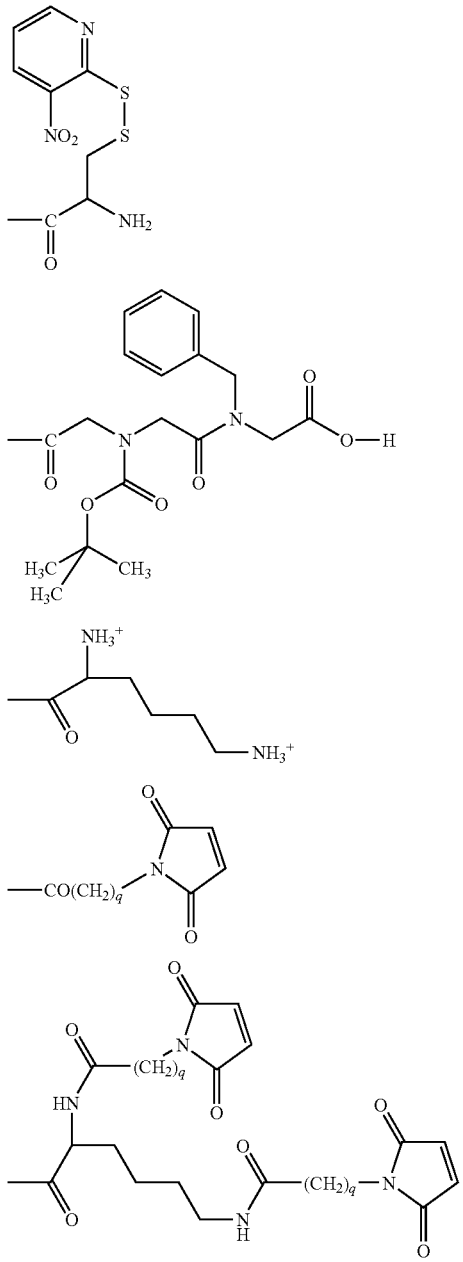
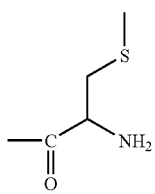
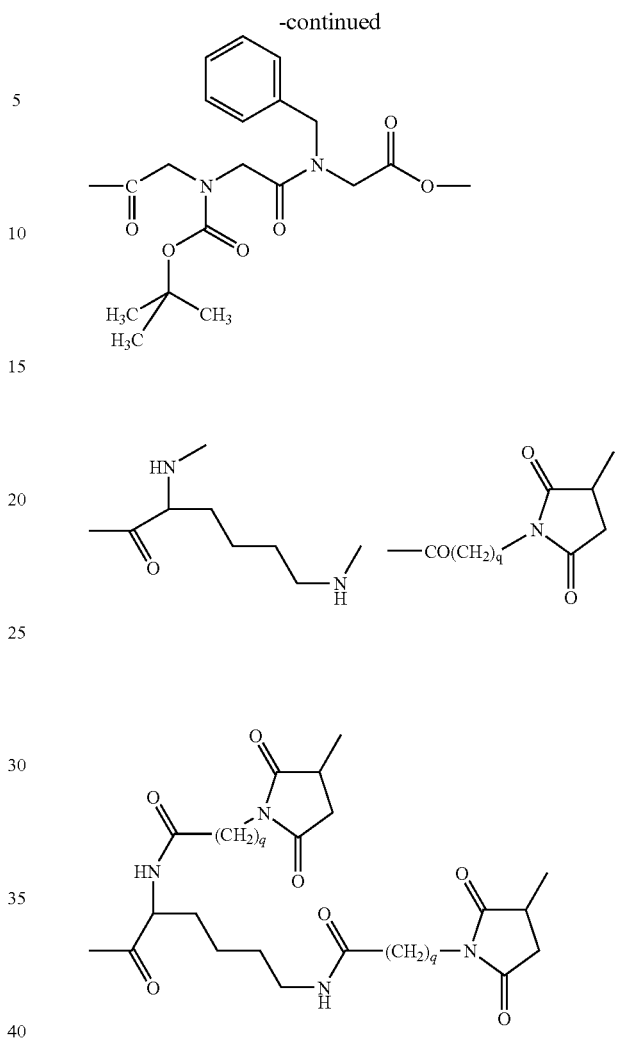

wherein q is an integer from 1 to 10;
or of one of the corresponding following formulae when a=1 and b=1 or 2:

wherein q is an integer from 1 to 10;

P is an effective group, optionally comprising a charge-carrying group, allowing spectroscopic detection of said functionalized carbon nanotube, selected from the group consisting of: a fluorophore: FITC, a chelating agent: DTPA, and an active molecule, liable to induce a biological effect, said active molecule being selected from the group consisting of: an amino acid, a peptide, a pseudopeptide, a polypeptide, a protein, an enzyme or an antibody, a nucleic acid, a carbohydrate, and a drug.

if appropriate at least one of Y, Z, or P groups, can be substituted by a capping group selected from the list consisting of: $CH_3CO-$, methyl, ethyl, or benzylcarbonyl, or a protecting group selected from the list consisting of: methyl, ethyl, benzyl, tert-butyl, trityl, 3-nitro-2-pyridylsulfenyl, tert-butyloxycarbonyl, fluorenylmethyloxycarbonyl, benzyloxycarbonyl, benzoyl, trimethylsilylethyloxycarbonyl, phtalimide, dimethylacetal, diethylacetal and, 1,3-dioxolane.

33. The complex according to claim 32, wherein X represents two different substituted pyrrolidine rings, provided that at least one of said pyrrolidine rings is substituted by at least one charge-carrying group, of the following general formula (I'):

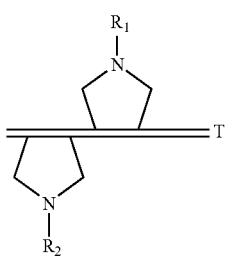

wherein T represents a carbon nanotube, $R_1$ and $R_2$ are different and represent, independently from each other, —H or a group of formula $-M-Y-(Z)_a-(P)_b$, at least one of $R_1$ and $R_2$ comprising a charge carrying group.

34. The complex according to claim 30, corresponding to the following general formula (II):

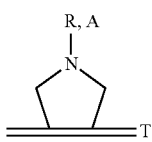

wherein T represents a carbon nanotube, A represents a charged molecule, and R represents a group of formula -M-W, and:

M is a spacer group from 1 to 100 atoms, said group being selected from $-(CH_2)_r-$ or $-(CH_2-CH_2-O)_r-CH_2-CH_2-$, wherein r is an integer from 1 to 20;

W is a charge-carrying group from 1 to 400 atoms.

35. The complex according to claim 33, corresponding to the following general formula (II'):

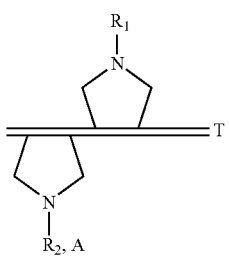

wherein T represents a carbon nanotube, A represents a charged molecule, and $R_1$ represents a group of formula $-M-Y-(Z)_a-(P)_b$, M, Y, Z, P, a and b, being as defined in claim 30, and, $R_2$ represents a group of formula -M-W, W being a charge-carrying group from 1 to 400 atoms.

36. The complex according to claim 4, wherein the charged molecule is selected from:

nucleic acids, selected from the group consisting of: RNA and DNA, comprising from 2 to $10^6$ nucleotides, peptides, polypeptides or proteins, comprising from 2 to 5000 amino acids, or carbohydrates selected from the group consisting of: glucosamine and chitosane, radionucleides, and cytotoxic molecules.

37. The complex according to claim 4, corresponding to the following formula:

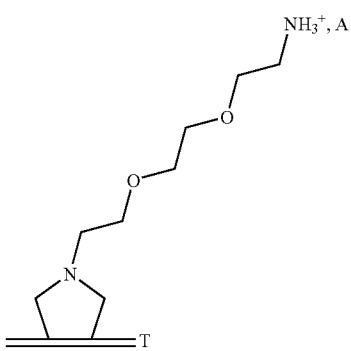

wherein T represents a carbon nanotube, and A represents a charged molecule, comprising at least one negative charge: DNA.

38. The complex according to claim 4, corresponding to the following formula:

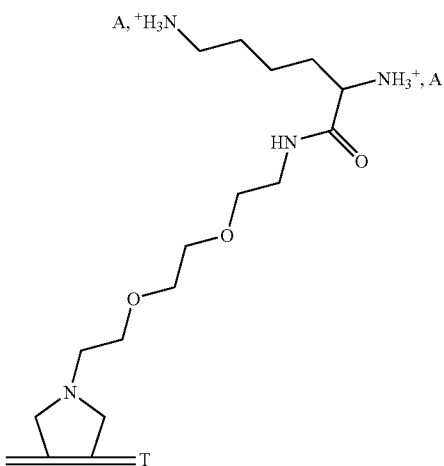

wherein T represents a carbon nanotube, and A represents a charged molecule, comprising at least one negative charge: DNA.

39. The complex according to claim 4, corresponding to the following formula:

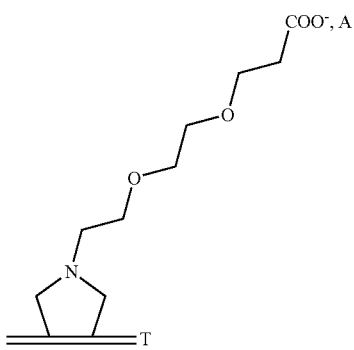

wherein T represents a carbon nanotube, and A represents a charged molecule comprising at least one positive charge.

40. A complex according to claim 4, corresponding to the following formula:

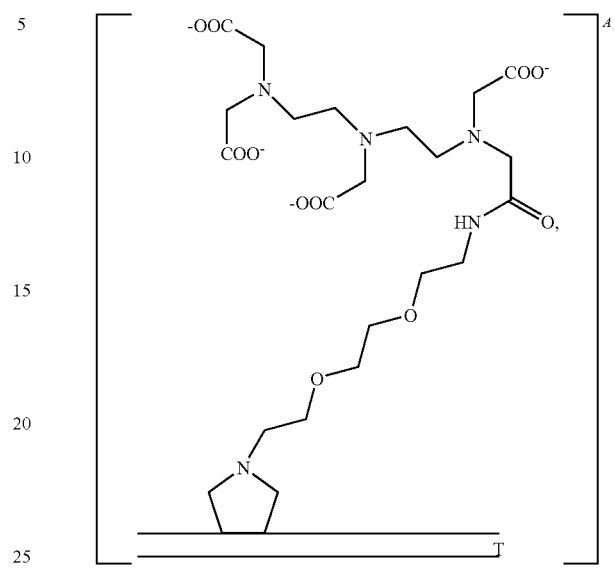

wherein T represents a carbon nanotube, and A represents a charged molecule comprising at least one positive charge.

41. A method of treatment of a patient in need thereof with the complex according to claim 4, for the delivery of the charged molecules into cells.

42. A pharmaceutical composition comprising as active substance a complex defined in claim 4, in association with an acceptable pharmaceutical carrier.

* * * * *